US011272887B2

(12) United States Patent
Stewart et al.

(10) Patent No.: US 11,272,887 B2
(45) Date of Patent: Mar. 15, 2022

(54) ELECTROANATOMICAL MAPPING TOOLS FACILITATED BY ACTIVATION WAVEFORMS

(71) Applicant: Boston Scientific Scimed Inc., Maple Grove, MN (US)

(72) Inventors: Brian Stewart, North Reading, MA (US); Nathan H. Bennett, Cambridge, MA (US); Mordechai Perlman, Cambridge, MA (US); Vasiliy E. Buharin, Arlington, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 59 days.

(21) Appl. No.: 15/955,537

(22) Filed: Apr. 17, 2018

(65) Prior Publication Data

US 2018/0296167 A1 Oct. 18, 2018

Related U.S. Application Data

(60) Provisional application No. 62/486,909, filed on Apr. 18, 2017.

(51) Int. Cl.
*A61B 5/0452* (2006.01)
*A61B 5/0432* (2006.01)
(Continued)

(52) U.S. Cl.
CPC ............ *A61B 5/7267* (2013.01); *A61B 5/287* (2021.01); *A61B 5/316* (2021.01); *A61B 5/339* (2021.01);
(Continued)

(58) Field of Classification Search
CPC ... A61B 5/044; A61B 5/04012; A61B 5/7475; A61B 5/726; A61B 5/0452; A61B 5/00;
(Continued)

(56) References Cited

U.S. PATENT DOCUMENTS

| 4,721,114 A | 1/1988 | DuFault et al. |
| 5,058,599 A | 10/1991 | Andersen |

(Continued)

FOREIGN PATENT DOCUMENTS

WO 2013123549 A1 8/2013

OTHER PUBLICATIONS

Anonymous: "Advanced Mapping and Navigation Modalities—Clinical Gate", Oct. 30, 2016, Retrieved from the Internet: https://clinicalgate.com/advanced-mapping-and-navigation-modalities/ Retrieved on Jun. 26, 2018.

(Continued)

*Primary Examiner* — Jon Eric C Morales
(74) *Attorney, Agent, or Firm* — Faegre Drinker Biddle & Reath LLP

(57) ABSTRACT

Systems and methods for facilitating display of cardiac information based on sensed electrical signals include a processing unit configured to receive a set of electrical signals; receive an indication of a measurement location corresponding to each electrical signal of the set of electrical signals; and generate an activation waveform corresponding to the set of electrical signals. Systems and methods disclosed herein may be configured to generate, based on the activation waveform, a representation of a cardiac electrical signal feature; and facilitate presentation, on a display device, of a cardiac map and the representation of the cardiac electrical signal feature.

20 Claims, 12 Drawing Sheets

(51) Int. Cl.
| | |
|---|---|
| *A61B 5/00* | (2006.01) |
| *G06T 19/00* | (2011.01) |
| *G06T 17/00* | (2006.01) |
| *G16H 50/20* | (2018.01) |
| *A61B 5/287* | (2021.01) |
| *A61B 5/316* | (2021.01) |
| *A61B 5/339* | (2021.01) |
| *A61B 5/349* | (2021.01) |

(52) U.S. Cl.
 CPC ............ *A61B 5/349* (2021.01); *A61B 5/6852* (2013.01); *A61B 5/725* (2013.01); *A61B 5/742* (2013.01); *G06T 17/00* (2013.01); *G06T 19/00* (2013.01); *G16H 50/20* (2018.01)

(58) Field of Classification Search
 CPC ......... A61B 5/024; A61B 5/0245; A61B 5/04; A61B 5/0432; A61B 5/4836; A61B 5/7264; A61B 5/743; A61B 5/0402; A61B 5/02405; A61B 5/06; A61B 5/066; A61B 5/042
 See application file for complete search history.

(56) References Cited

U.S. PATENT DOCUMENTS

| | | | |
|---|---|---|---|
| 6,070,094 | A | 5/2000 | Swanson et al. |
| 6,233,491 | B1 | 5/2001 | Kordis et al. |
| 6,236,883 | B1 | 5/2001 | Ciaccio et al. |
| 6,735,465 | B2 | 5/2004 | Panescu |
| 7,515,954 | B2 | 4/2009 | Harlev et al. |
| 8,103,338 | B2 | 1/2012 | Harlev et al. |
| 8,229,545 | B2 | 7/2012 | Afonso |
| 8,428,700 | B2 | 4/2013 | Harlev et al. |
| 8,615,287 | B2 | 12/2013 | Harlev et al. |
| 8,647,284 | B2 | 2/2014 | Afonso |
| 8,838,216 | B2 | 9/2014 | Francis et al. |
| 8,948,837 | B2 | 2/2015 | Harlev et al. |
| 9,078,573 | B2 | 7/2015 | Ramanathan et al. |
| 9,265,951 | B2 | 2/2016 | Sweeney |
| 2007/0177801 | A1 | 8/2007 | Kawamoto et al. |
| 2009/0069704 | A1 | 3/2009 | MacAdam et al. |
| 2011/0206256 | A1 | 8/2011 | Ramanathan et al. |
| 2013/0085406 | A1* | 4/2013 | Gunderson ............ A61B 5/339 600/518 |
| 2014/0005563 | A1* | 1/2014 | Ramanathan ...... A61B 5/04012 600/523 |
| 2015/0065836 | A1 | 3/2015 | Thakur et al. |
| 2015/0208938 | A1 | 7/2015 | Houben et al. |
| 2015/0216438 | A1 | 8/2015 | Bokan et al. |
| 2015/0366476 | A1 | 12/2015 | Laughner et al. |
| 2017/0079539 | A1 | 3/2017 | Chauhan et al. |
| 2017/0156616 | A1 | 6/2017 | Talkachova et al. |
| 2017/0224238 | A1 | 8/2017 | Arunachalam et al. |
| 2018/0296108 | A1 | 10/2018 | Stewart et al. |
| 2018/0296113 | A1 | 10/2018 | Stewart et al. |

OTHER PUBLICATIONS

International Search Report and Written Opinion issued in PCT/US2018/027909, dated Jun. 28, 2018, 10 pages.
International Search Report and Written Opinion issued in PCT/US2018/027927, dated Jul. 16, 2018, 15 pages.
Przemyslaw Zajac et al., "EJMT 4(13) 2016@BULLET European Journal of Medical Technologies Corresponding address: Electroanatomic Mapping System—the useful tool for electrophysilogy", Dec. 31, 2016.
International Preliminary Report on Patentability issued in PCT/US2018/027909, dated Oct. 31, 2019, 7 pages.
International Preliminary Report on Patentability issued in PCT/US2018/027927, dated Oct. 31, 2019, 9 pages.

* cited by examiner

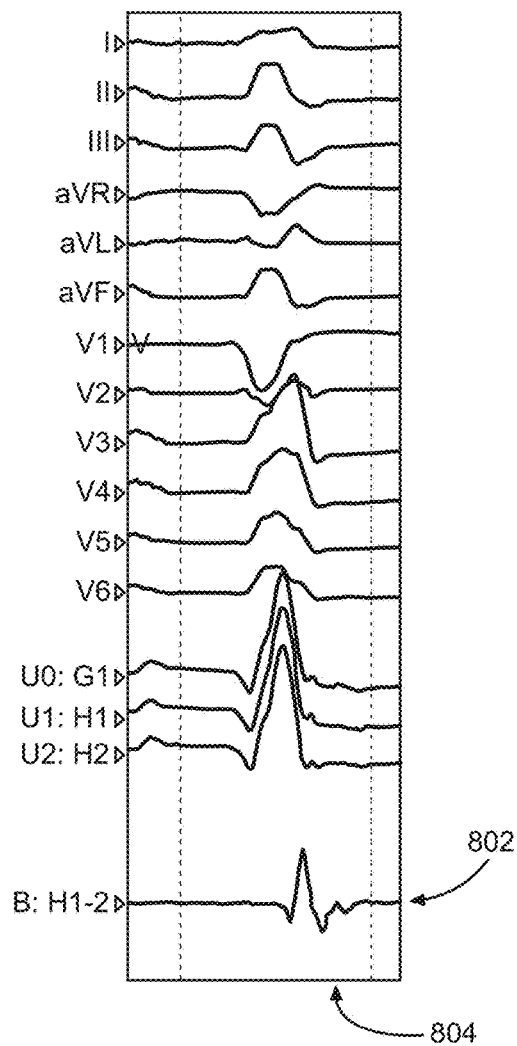 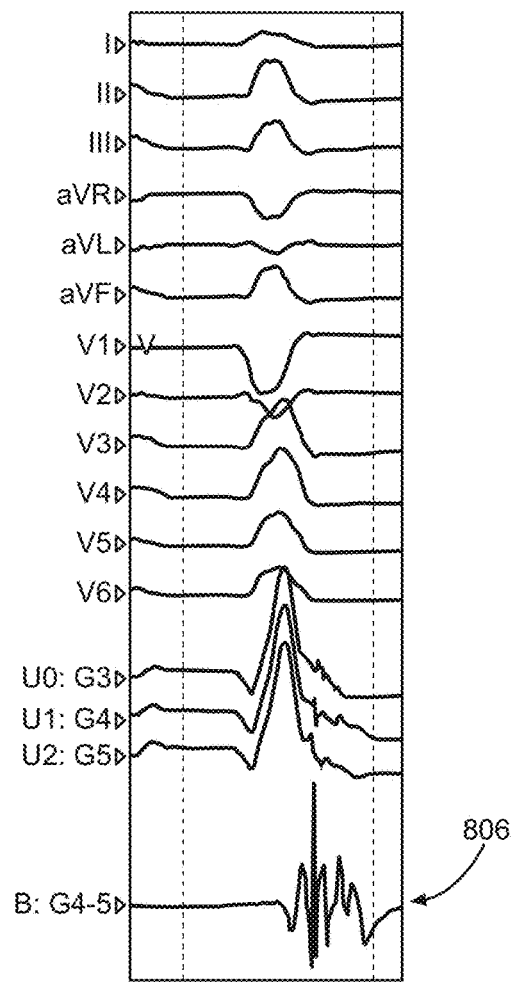
FIG. 8A  FIG. 8B

ELECTROANATOMICAL MAPPING TOOLS FACILITATED BY ACTIVATION WAVEFORMS

CROSS-REFERENCE TO RELATED APPLICATION

This application claims priority to Provisional Application No. 62/486,909, filed Apr. 18, 2017, which is herein incorporated by reference in its entirety.

TECHNICAL FIELD

The present disclosure relates to medical systems and methods for mapping an anatomical space of the body. More specifically, the disclosure relates to systems and methods for cardiac mapping.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Conventional three-dimensional (3D) mapping techniques include contact mapping and non-contact mapping, and may employ a combination of contact and non-contact mapping. In both techniques, one or more catheters are advanced into the heart. With some catheters, once in the chamber, the catheter may be deployed to assume a 3D shape. In contact mapping, physiological signals resulting from the electrical activity of the heart are acquired with one or more electrodes located at the catheter distal tip after determining that the tip is in stable and steady contact with the endocardium surface of a particular heart chamber. In non-contact-based mapping systems, using the signals detected by the non-contact electrodes and information on chamber anatomy and relative electrode location, the system provides physiological information regarding the endocardium of the heart chamber. Location and electrical activity is usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm.

In many conventional mapping systems, the clinician visually inspects or examines the captured electrograms (EGMs), which increases examination time and cost. During an automatic electro-anatomical mapping process, however, approximately 6,000 to 20,000 intracardiac electrograms (EGMs) may be captured, which does not lend itself to being manually inspected in full by a clinician (e.g., a physician) for a diagnostic assessment, EGM categorization, and/or the like. Typically mapping systems extract scalar values from each EGM to construct voltage, activation, or other map types to depict overall patterns of activity within the heart. While maps reduce the need to inspect the captured EGMs, they also condense the often complex and useful information in the EGMs. Furthermore, maps may be misleading due to electrical artifacts or inappropriate selection of features such as activation times. Additionally, due to the complex nature of conventional techniques, cardiac maps often are not suitable for accurate and efficient interpretation.

SUMMARY

In an Example 1, a system for facilitating display of cardiac information based on sensed electrical signals, the system comprising: a processing unit configured to: receive a set of electrical signals; receive an indication of a measurement location corresponding to each electrical signal of the set of electrical signals; generate an activation waveform corresponding to the set of electrical signals; generate, based on the activation waveform, a representation of a cardiac electrical signal feature; and facilitate presentation, on a display device, of a cardiac map and the representation of the cardiac electrical signal feature.

In an Example 2, the system of Example 1, the representation of the cardiac electrical signal feature comprising a representation of an activation region, the activation region comprising a region of tissue in which one or more activations are identified within a specified time period.

In an Example 3, the system of Example 2, the representation of the activation region comprising a border that is presented using a color that is different than one or more colors adjacent to the border, wherein the one or more adjacent colors are used to represent one or more annotations.

In an Example 4, the system of any of Examples 1-3, the map comprising a dynamic map, wherein the processing unit is further configured to cause the display device to sequentially present instances of the map corresponding to sequential time periods, wherein a location of the activation region changes throughout the sequential instances of the map, thereby representing a propagation of the activation waveform.

In an Example 5, the system of any of the preceding Examples, the plurality of electrical signals comprising a plurality of intracardiac electrograms (EGMs).

In an Example 6, the system of any of the preceding Examples, wherein the map comprises at least one of a voltage map, an activation map, and a fractionation map.

In an Example 7, the system of any of the preceding Examples, the cardiac electrical signal feature comprising at least one of an activation time, a minimum voltage value, a maximum voltages value, a maximum negative time-derivative of voltage, an instantaneous potential, a voltage amplitude, a dominant frequency, and a peak-to-peak voltage.

In an Example 8, the system of Example 1, wherein the processing unit is further configured to automatically classify, based on the activation waveform, each electrical signal of the set of electrical signals.

In an Example 9, the system of Example 8, wherein the processing unit is further configured to: receive a search query, the search query comprising an identification of a classification; identify a subset of the set of electrical signals having the classification; and facilitate modification of the presentation of the cardiac map, via the display device, based on information associated with the identified subset of electrical signals having the classification.

In an Example 10, the system of either of Examples 1 or 8, wherein the processing unit is further configured to: receive an indication of a user selection of one or more electrical signal characteristics; identify a subset of the set of electrical signals having the one or more selected electrical signal characteristics; generate, based on the identified subset of electrical signals, a spatial distribution of electrical signals having the one or more selected electrical signal characteristics; and facilitate presentation, on the display device, of a representation of the spatial distribution.

In an Example 11, the system of Example 10, wherein the one or more selected electrical signal characteristics includes double-potentials, fractionation, multi-component, activation, lack of activation, split potentials, and/or QS signal morphology.

In an Example 12, a method of facilitating display of cardiac information, the method comprising: receiving a set of electrical signals; receiving an indication of a measurement location corresponding to each of the set of electrical signals; generating an activation waveform corresponding to the set of electrical signals; generating, based on the activation waveform, a representation of a cardiac electrical signal feature; and facilitating presentation, on a display device, of a cardiac map and the representation of the cardiac electrical signal feature.

In an Example 13, the method of Example 12, the representation of the cardiac signal feature comprising a representation of an activation region, the activation region comprising a region of tissue in which one or more activations are identified within a specified time period.

In an Example 14, the method of Example 13, the map comprising a dynamic map, the method further comprising causing the display device to sequentially present instances of the map corresponding to sequential time periods, wherein a location of the activation region changes throughout the sequential instances of the map, thereby representing a propagation of the activation waveform.

In an Example 15, the method of Example 12, further comprising automatically classifying, based on the activation waveform, each electrical signal of the set of electrical signals.

In an Example 16, a system for facilitating display of cardiac information based on sensed electrical signals, the system comprising: a display device configured to present a cardiac map of a cardiac structure; and a processing unit configured to: receive a set of electrical signals; receive an indication of a measurement location corresponding to each electrical signal of the set of electrical signals; generate an activation waveform corresponding to the set of electrical signals; generate, based on the activation waveform, a representation of a cardiac electrical signal feature; and facilitate presentation, on the display device, of the cardiac map and the representation of the cardiac electrical signal feature.

In an Example 17, the system of Example 16, the representation of the cardiac electrical signal feature comprising a representation of an activation region, the activation region comprising a region of tissue in which one or more activations are identified within a specified time period.

In an Example 18, the system of Example 17, the representation of the activation region comprising a border that is presented using a color that is different than one or more colors adjacent to the border, wherein the one or more adjacent colors are used to represent one or more annotations.

In an Example 19, the system of Example 16, the map comprising a dynamic map, wherein the processing unit is further configured to cause the display device to sequentially present instances of the map corresponding to sequential time periods, wherein a location of the activation region changes throughout the sequential instances of the map, thereby representing a propagation of the activation waveform.

In an Example 20, the system of Example 16, the plurality of electrical signals comprising a plurality of intracardiac electrograms (EGMs).

In an Example 21, the system of Example 16, wherein the map comprises at least one of a voltage map, an activation map, and a fractionation map.

In an Example 22, the system of Example 16, the cardiac electrical signal feature comprising at least one of an activation time, a minimum voltage value, a maximum voltages value, a maximum negative time-derivative of voltage, an instantaneous potential, a voltage amplitude, a dominant frequency, and a peak-to-peak voltage.

In an Example 23, the system of Example 16, wherein the processing unit is further configured to automatically classify, based on the activation waveform, each electrical signal of the set of electrical signals.

In an Example 24, the system of Example 23, wherein the processing unit is further configured to: receive a search query, the search query comprising an identification of a classification; identify a subset of the set of electrical signals having the classification; and facilitate modification of the presentation of the cardiac map, via the display device, based on information associated with the identified subset of electrical signals having the classification.

In an Example 25, the system of Example 16, wherein the processing unit is further configured to: receive an indication of a user selection of one or more electrical signal characteristics; identify a subset of the set of electrical signals having the one or more selected electrical signal characteristics; generate, based on the identified subset of electrical signals, a spatial distribution of electrical signals having the one or more selected electrical signal characteristics; and facilitate presentation, on the display device, of a representation of the spatial distribution.

In an Example 26, the system of Example 25, wherein the one or more selected electrical signal characteristics includes double-potentials, fractionation, multi-component, activation, lack of activation, split potentials, and/or QS signal morphology.

In an Example 27, a system for facilitating display of cardiac information based on sensed electrical signals, the system comprising: a display device configured to present a cardiac map of a cardiac structure; and a processing unit configured to: receive a set of electrical signals; receive an indication of a measurement location corresponding to each electrical signal of the set of electrical signals; generate an activation waveform corresponding to the set of electrical signals; classify, based on the activation waveform, each electrical signal of the set of electrical signals; receive an indication of a user selection of one or more electrical signal characteristics; identify a subset of the set of electrical signals having the one or more selected electrical signal characteristics; generate, based on the identified subset of electrical signals, a spatial distribution of electrical signals having the one or more selected electrical signal characteristics; and facilitate presentation, on the display device, of the cardiac map and a representation of the spatial distribution.

In an Example 28, the system of Example 27, wherein the one or more selected electrical signal characteristics include double-potentials, fractionation, multi-component, activation, lack of activation, split potentials, and/or QS signal morphology.

In an Example 29, a method of facilitating display of cardiac information, the method comprising: receiving a set of electrical signals; receiving an indication of a measurement location corresponding to each of the set of electrical signals; generating an activation waveform corresponding to the set of electrical signals; generating, based on the activation waveform, a representation of a cardiac electrical signal feature; and facilitating presentation, on a display device, of a cardiac map and the representation of the cardiac electrical signal feature.

In an Example 30, the method of Example 29, the representation of the cardiac signal feature comprising a representation of an activation region, the activation region comprising a region of tissue in which one or more activations are identified within a specified time period.

In an Example 31, the method of Example 30, the map comprising a dynamic map, the method further comprising causing the display device to sequentially present instances of the map corresponding to sequential time periods, wherein a location of the activation region changes throughout the sequential instances of the map, thereby representing a propagation of the activation waveform.

In an Example 32, the method of Example 29, further comprising automatically classifying, based on the activation waveform, each electrical signal of the set of electrical signals.

In an Example 33, the method of Example 32, further comprising: receiving a search query, the search query comprising an identification of a classification; identifying a subset of the set of electrical signals having the classification; and facilitating modification of the presentation of the cardiac map, via the display device, based on information associated with the identified subset of electrical signals having the classification.

In an Example 34, the method of Example 29, further comprising: receiving an indication of a user selection of one or more electrical signal characteristics; identifying a subset of the set of electrical signals having the one or more selected electrical signal characteristics; generating, based on the identified subset of electrical signals, a spatial distribution of electrical signals having the one or more selected electrical signal characteristics; and facilitating presentation, on the display device, of a representation of the spatial distribution.

In an Example 35, the method of Example 34, wherein the one or more selected electrical signal characteristics includes double-potentials, fractionation, multi-component, activation, lack of activation, split potentials, and/or QS signal morphology.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF THE DRAWINGS

FIGS. 8A and 8B depict illustrative graphical representation of electrical signals received from a mapping catheter, in accordance with embodiments of the subject matter disclosed herein.

Figure 1:
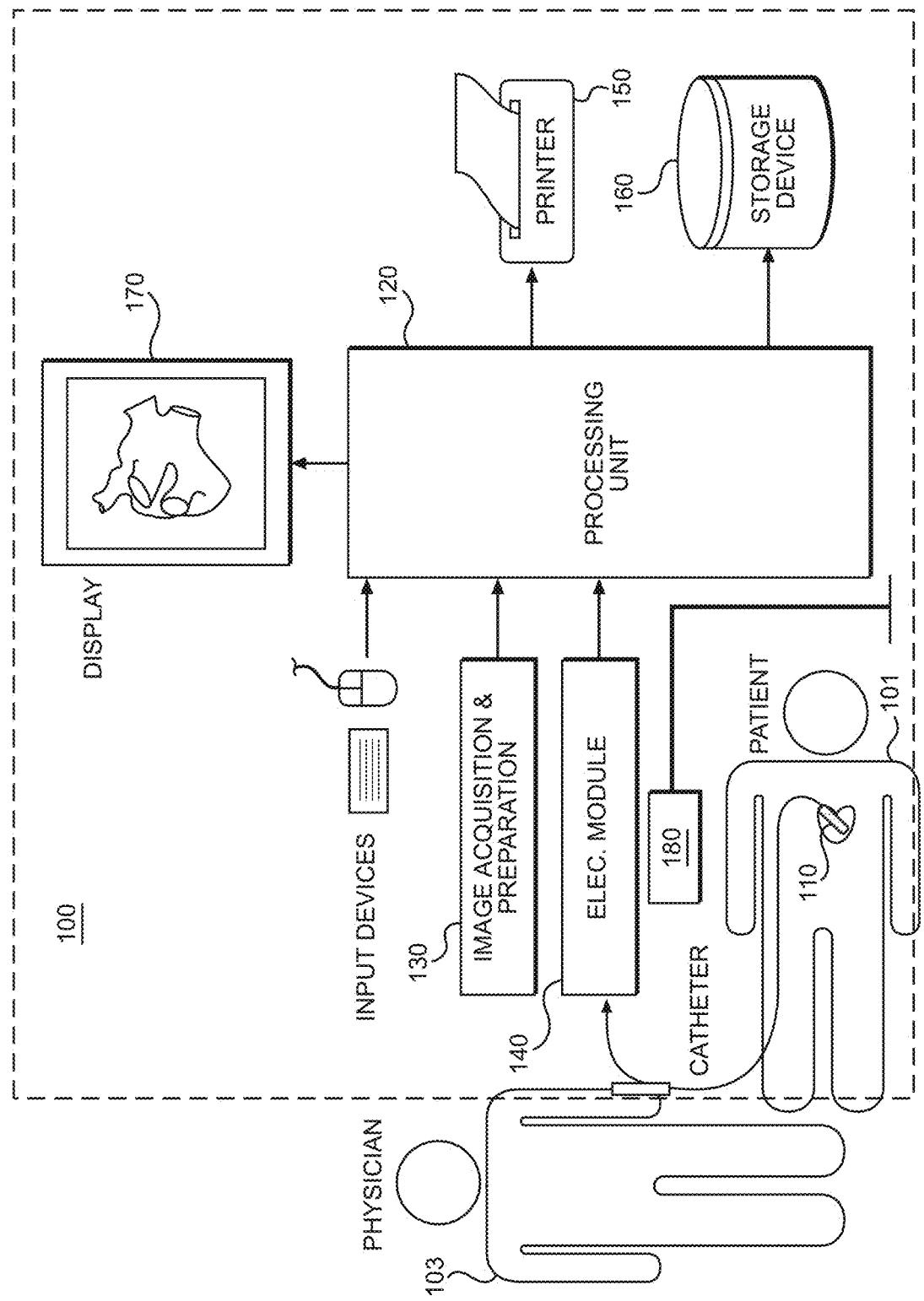
FIG. 1 is a conceptual schematic diagram depicting an illustrative cardiac mapping system, in accordance with embodiments of the subject matter disclosed herein.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

DETAILED DESCRIPTION

Embodiments of systems and methods described herein facilitate processing sensed cardiac electrical signals to return the per-sample "probability" of tissue activation by generating activation waveforms. An activation waveform is a set of activation waveform values and may include, for example, a set of discrete activation waveform values (e.g., a set of activation waveform values, a set of activation time annotations, etc.), a function defining an activation waveform curve, and/or the like. Accordingly, in embodiments, the term "activation waveform" may include a "filtered activation waveform," as described below. Similarly, as explained herein, embodiments of systems and methods described herein facilitate generating other types of annotation waveforms. An annotation waveform is a set of annotation waveform values and may include, for example, a set of discrete activation annotation values (e.g., a set of annotation waveform values, a set of time annotations, etc.), a function defining an annotation waveform curve, and/or the like. Accordingly, in embodiments, the term "annotation waveform" may include a "filtered annotation waveform." Although much of the description herein relates to activation waveforms and activation histograms, this is only for the purpose of clarity of description, and it is to be understood that any number of different aspects of embodiments described in relation to activation waveforms and/or activation histograms may apply more generally to annotation waveforms and/or annotation histograms, respectively.

Embodiments facilitate finding meaningful deflections while rejecting noises and artifacts. In embodiments, the annotation waveform may be displayed, used to present an activation waveform propagation map, used to facilitate diagnoses, used to facilitate classification of electrical signals, and/or the like. According to embodiments, to perform aspects of embodiments of the methods described herein, the cardiac electrical signals may be obtained from a mapping catheter (e.g., associated with a mapping system), a recording system, a coronary sinus (CS) catheter or other reference catheter, an ablation catheter, a memory device (e.g., a local memory, a cloud server, etc.), a communication component, a medical device (e.g., an implantable medical device, an external medical device, a telemetry device, etc.), and/or the like.

As the term is used herein, a sensed cardiac electrical signal may refer to one or more sensed signals. Each cardiac electrical signal may include a number of intracardiac electrograms (EGMs) sensed within a patient's heart, and may include any number of features that may be ascertained by aspects of the system 100. Examples of cardiac electrical signal features include, but are not limited to, activation times, activations, activation waveforms, filtered activation waveforms, minimum voltage values, maximum voltages values, maximum negative time-derivatives of voltages, instantaneous potentials, voltage amplitudes, dominant frequencies, peak-to-peak voltages, and/or the like. A cardiac electrical signal feature may refer to one or more features extracted from one or more cardiac electrical signals, derived from one or more features that are extracted from one or more cardiac electrical signals, and/or the like. Additionally, a representation, on a cardiac and/or a surface map, of a cardiac electrical signal feature may represent one or more cardiac electrical signal features, an interpolation of a number of cardiac electrical signal features, and/or the like.

Each cardiac signal also may be associated with a set of respective position coordinates that corresponds to the location at which the cardiac electrical signal was sensed. Each of the respective position coordinates for the sensed cardiac signals may include three-dimensional Cartesian coordinates, polar coordinates, and/or the like. In embodiments, other coordinate systems can be used. In embodiments, an arbitrary origin is used and the respective position coordinates refer to positions in space relative to the arbitrary origin. Since, in embodiments, the cardiac signals may be sensed on the cardiac surfaces, the respective position coordinates may be on the endocardial surface, epicardial surface, in the mid-myocardium of the patient's heart, and/or in the vicinity of one of one of these.

FIG. 1 shows a schematic diagram of an exemplary embodiment of a cardiac mapping system 100. As indicated above, embodiments of the subject matter disclosed herein may be implemented in a mapping system (e.g., the mapping system 100), while other embodiments may be implemented in an ablation system, a recording system, a computer analysis system, and/or the like. The mapping system 100 includes a moveable catheter 110 having multiple spatially distributed electrodes. During a signal-acquisition stage of a cardiac mapping procedure, the catheter 110 is displaced to multiple locations within the heart chamber into which the catheter 110 is inserted. In some embodiments the distal end of the catheter 110 is fitted with multiple electrodes spread somewhat uniformly over the catheter. For example, the electrodes may be mounted on the catheter 110 following a 3D olive shape, a basket shape, and/or the like. The electrodes are mounted on a device capable of deploying the electrodes into the desired shape while inside the heart, and retracting the electrodes when the catheter is removed from the heart. To allow deployment into a 3D shape in the heart, electrodes may be mounted on a balloon, shape memory material such as Nitinol, actuable hinged structure, and/or the like. According to embodiments, the catheter 110 may be a mapping catheter, an ablation catheter, a diagnostic catheter, a CS catheter, and/or the like. For example, aspects of embodiments of the catheter 110, the electrical signals obtained using the catheter 110, and subsequent processing of the electrical signals, as described herein, may also be applicable in implementations having a recording system, ablation system, and/or any other system having a catheter with electrodes that may be configured to obtain cardiac electrical signals.

At each of the locations to which the catheter 110 is moved, the catheter's multiple electrodes acquire signals resulting from the electrical activity in the heart. Consequently, reconstructing and presenting to a user (such as a doctor and/or technician) physiological data pertaining to the heart's electrical activity may be based on information acquired at multiple locations, thereby providing a more accurate and faithful reconstruction of physiological behavior of the endocardium surface. The acquisition of signals at multiple catheter locations in the heart chamber enables the catheter to effectively act as a "mega-catheter" whose effective number of electrodes and electrode span is proportional to the product of the number of locations in which signal acquisition is performed and the number of electrodes the catheter has.

To enhance the quality of the reconstructed physiological information at the endocardium surface, in some embodiments the catheter 110 is moved to more than three locations (for example, more than 5, 10, or even 50 locations) within the heart chamber. Further, the spatial range over which the catheter is moved may be larger than one third (⅓) of the diameter of the heart cavity (for example, larger than 35%, 40%, 50% or even 60% of the diameter of the heart cavity). Additionally, in some embodiments the reconstructed physiological information is computed based on signals measured over several heart beats, either at a single catheter location within the heart chamber or over several locations. In circumstances where the reconstructed physiological information is based on multiple measurements over several heart beats, the measurements may be synchronized with one another so that the measurement are performed at approximately the same phase of the heart cycle. The signal measurements over multiple beats may be synchronized based on features detected from physiological data such as surface electrocardiograms (ECGs) and/or intracardiac electrograms (EGMs).

The cardiac mapping system 100 further includes a processing unit 120 which performs several of the operations pertaining to the mapping procedure, including the reconstruction procedure to determine the physiological information at the endocardium surface (e.g., as described above) and/or within a heart chamber. The processing unit 120 also may perform a catheter registration procedure. The processing unit 120 also may generate a 3D grid used to aggregate the information captured by the catheter 110 and to facilitate display of portions of that information.

The location of the catheter 110 inserted into the heart chamber can be determined using a conventional sensing and tracking system 180 that provides the 3D spatial coordinates of the catheter and/or its multiple electrodes with respect to the catheter's coordinate system as established by the sensing and tracking system. These 3D spatial locations may be used in building the 3D grid. Embodiments of the system 100 may use a hybrid location technology that combines impedance location with magnetic location technology. This combination may enable the system 100 to accurately track catheters that are connected to the system 100. Magnetic location technology uses magnetic fields generated by a localization generator positioned under the patient table to track catheters with magnetic sensors. Impedance location technology may be used to track catheters that may not be equipped with a magnetic location sensor, and may utilize surface ECG patches.

In embodiments, to perform a mapping procedure and reconstruct physiological information on the endocardium surface, the processing unit 120 may align the coordinate system of the catheter 110 with the endocardium surface's coordinate system. The processing unit 110 (or some other processing component of the system 100) may determine a coordinate system transformation function that transforms the 3D spatial coordinates of the catheter's locations into coordinates expressed in terms of the endocardium surface's coordinate system, and/or vice-versa. In embodiments, such a transformation may not be necessary, as embodiments of the 3D grid described herein may be used to capture contact and non-contact EGMs, and select mapping values based on statistical distributions associated with nodes of the 3D grid. The processing unit 120 also may perform post-processing operations on the physiological information to extract and display useful features of the information to the operator of the system 100 and/or other persons (e.g., a physician).

According to embodiments, the signals acquired by the multiple electrodes of catheter 110 are passed to the processing unit 120 via an electrical module 140, which may include, for example, a signal conditioning component. The electrical module 140 receives the signals communicated from the catheter 110 and performs signal enhancement operations on the signals before they are forwarded to the processing unit 120. The electrical module 140 may include signal conditioning hardware, software, and/or firmware that may be used to amplify, filter and/or sample intracardiac potential measured by one or more electrodes. The intracardiac signals typically have a maximum amplitude of 60 mV, with a mean of a few millivolts.

In some embodiments the signals are bandpass filtered in a frequency range (e.g., 0.5-500 Hz) and sampled with analog to digital converters (e.g., with 15-bit resolution at 1 kHz). To avoid interference with electrical equipment in the room, the signal may be filtered to remove the frequency corresponding to the power supply (e.g., 60 Hz). Other types of signal processing operations such as spectral equalization, automatic gain control, etc. may also take place. For example, in embodiments, the intracardiac signals may be unipolar signals, measured relative to a reference (which may be a virtual reference) such as, for example, a coronary sinus catheter or Wilson's Central Terminal (WCT), from which the signal processing operations may compute differences to generate multipolar signals (e.g., bipolar signals, tripolar signals, etc.). The signals may be otherwise processed (e.g., filtered, sampled, etc.) before and/or after generating the multipolar signals. The resultant processed signals are forwarded by the module 140 to the processing unit 120 for further processing.

As further shown in FIG. 1, the cardiac mapping system 100 also may include peripheral devices such as a printer 150 and/or display device 170, both of which may be interconnected to the processing unit 120. Additionally, the mapping system 100 includes storage device 160 that may be used to store data acquired by the various interconnected modules, including the volumetric images, raw data measured by electrodes and/or the resultant endocardium representation computed therefrom, the partially computed transformations used to expedite the mapping procedures, the reconstructed physiological information corresponding to the endocardium surface, and/or the like.

In embodiments, the processing unit 120 may be configured to automatically improve the accuracy of its algorithms by using one or more artificial intelligence (i.e., machine-learning) techniques, classifiers, and/or the like. In embodiments, for example, the processing unit may use one or more supervised and/or unsupervised techniques such as, for example, support vector machines (SVMs), k-nearest neighbor techniques, artificial neural networks, and/or the like. In embodiments, classifiers may be trained and/or adapted using feedback information from a user, other metrics, and/or the like.

The illustrative cardiac mapping system 100 shown in FIG. 1 is not intended to suggest any limitation as to the scope of use or functionality of embodiments of the present disclosure. Neither should the illustrative cardiac mapping system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the subject matter disclosed herein. For example, the electrical module 140 may be integrated with the processing unit 120. Additionally, or alternatively, aspects of embodiments of the cardiac mapping system 100 may be implemented in a computer analysis system configured to receive cardiac electrical signals and/or other information from a memory device (e.g., a cloud server, a mapping system memory, etc.), and perform aspects of embodiments of the methods described herein for processing cardiac information (e.g., determining annotation waveforms, etc.). That is, for example, a computer analysis system may include a processing unit 120, but not a mapping catheter.

Figure 2:
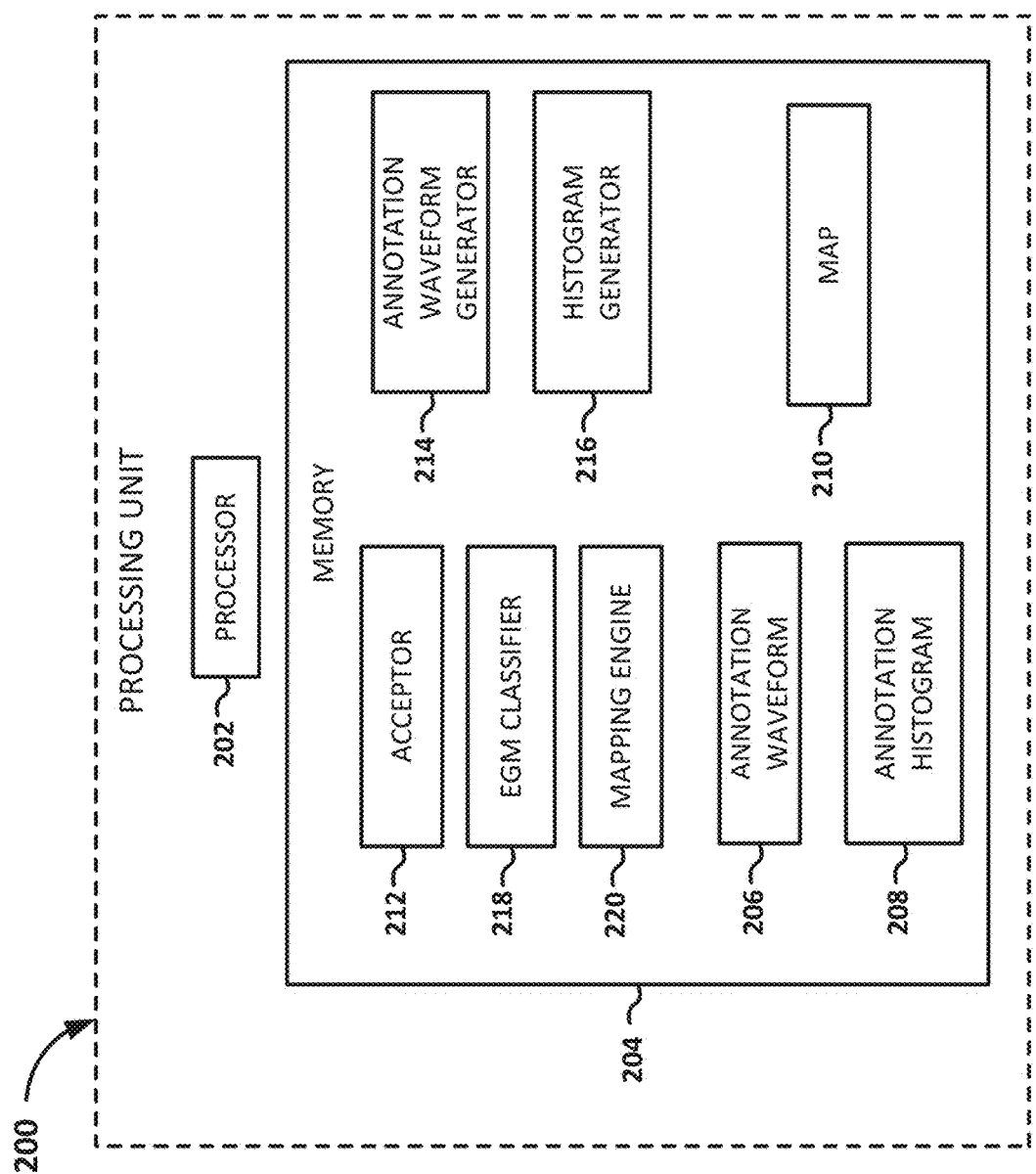
FIG. 2 is a block diagram depicting an illustrative processing unit for use with a cardiac mapping system, in accordance with embodiments of the subject matter disclosed herein.

FIG. 2 is a block diagram of an illustrative processing unit 200, in accordance with embodiments of the disclosure. The processing unit 200 may be, be similar to, include, or be included in the processing unit 120 depicted in FIG. 1. As shown in FIG. 2, the processing unit 200 may be implemented on a computing device that includes a processor 202 and a memory 204. Although the processing unit 200 is referred to herein in the singular, the processing unit 200 may be implemented in multiple instances (e.g., as a server cluster), distributed across multiple computing devices, instantiated within multiple virtual machines, and/or the like. One or more components for facilitating cardiac mapping may be stored in the memory 204. In embodiments, the processor 202 may be configured to instantiate the one or more components to generate an annotation waveform 206, an annotation histogram 208, and a cardiac map 210, any one or more of which may be stored in the memory 204.

As is further depicted in FIG. 2, the processing unit 200 may include an acceptor 212 configured to receive electrical signals from a mapping catheter (e.g., the mapping catheter 110 depicted in FIG. 1). The measured electrical signals may include a number of intracardiac electrograms (EGMs) sensed within a patient's heart. The acceptor 212 may also receive an indication of a measurement location corresponding to each of the electrical signals. In embodiments, the acceptor 212 may be configured to determine whether to accept the electrical signals that have been received. The acceptor 212 may utilize any number of different components and/or techniques to determine which electrical signals or beats to accept, such as filtering, beat matching, morphology analysis, positional information (e.g., catheter motion), respiration gating, and/or the like.

The accepted electrical signals are received by an annotation waveform generator 214 that is configured to extract at least one annotation feature from each of the electrical signals, in cases in which the electrical signal includes an annotation feature to extract. In embodiments, the at least one annotation feature includes at least one value corresponding to at least one annotation metric. The at least one feature may include at least one event, where the at least one event includes the at least one value corresponding to the at least one metric and/or at least one corresponding time (a corresponding time does not necessarily exist for each annotation feature). According to embodiments, the at least one metric may include, for example, an activation time, minimum voltage value, maximum voltage value, maximum negative time-derivative of voltage, an instantaneous potential, a voltage amplitude, a dominant frequency, a peak-to-peak voltage, an activation duration, and/or the like. According to embodiments, the annotation waveform generator 214 may be configured to detect activations and to generate an annotation waveform 206, which may be, for example, an activation waveform.

As shown in FIG. 2, the processing unit 200 includes a histogram generator 216 that is configured to generate an annotation histogram 208 having a number of bins within which annotations from electrograms (EGMs) are included. The processing unit 200, using the histogram generator 216, may be configured to aggregate a set of annotation features by including each of the features and/or EGMs in a histogram. For example, the histogram generator 216 may be configured to aggregate the set of activation features by assigning a confidence level to each event corresponding to an activation feature; determining a weighted confidence level associated with each event; and including the weighted confidence levels in a histogram. The processing unit includes an electrogram (EGM) classifier 218 that is configured to classify EGMs according to any number of different classifications based, for example, on characteristic of the EGM, the annotation waveform 206, annotation histogram 208, and/or the like. Additionally, the processing unit 200 includes a mapping engine 220 that is configured to facilitate presentation of a map 210 corresponding to a cardiac surface based on the electrical signals. In embodiments, the map 210 may include a voltage map, an activation map, a fractionation map, velocity map, confidence map, and/or the like.

The illustrative processing unit 200 shown in FIG. 2 is not intended to suggest any limitation as to the scope of use or functionality of embodiments of the present disclosure. Neither should the illustrative processing unit 200 be interpreted as having any dependency or requirement related to any single component or combination of components illustrated therein. Additionally, any one or more of the components depicted in FIG. 2 may be, in embodiments, integrated with various ones of the other components depicted therein (and/or components not illustrated), all of which are considered to be within the ambit of the subject matter disclosed herein. For example, the acceptor 212 may be integrated with the EGM classifier 218 and/or the mapping engine 220. In embodiments, the processing unit 200 may not include an acceptor 212, while in other embodiments, the acceptor 212 may be configured to receive electrical signals from a memory device, a communication component, and/or the like.

Additionally, the processing unit 200 may (alone and/or in combination with other components of the system 100 depicted in FIG. 1, and/or other components not illustrated) perform any number of different functions and/or processes associated with cardiac mapping (e.g., triggering, blanking, field mapping, etc.) such as, for example, those described in U.S. Pat. No. 8,428,700, entitled "ELECTROANATOMICAL MAPPING;" U.S. Pat. No. 8,948,837, entitled "ELEC- TROANATOMICAL MAPPING;" U.S. Pat. No. 8,615,287, entitled "CATHETER TRACKING AND ENDOCARDIUM REPRESENTATION GENERATION;" U.S. Patent Publication 2015/0065836, entitled "ESTIMATING THE PREVALENCE OF ACTIVATION PATTERNS IN DATA SEGMENTS DURING ELECTROPHYSIOLOGY MAPPING;" U.S. Pat. No. 6,070,094, entitled "SYSTEMS AND METHODS FOR GUIDING MOVABLE ELECTRODE ELEMENTS WITHIN MULTIPLE-ELECTRODE STRUCTURE;" U.S. Pat. No. 6,233,491, entitled "CARDIAC MAPPING AND ABLATION SYSTEMS;" U.S. Pat. No. 6,735,465, entitled "SYSTEMS AND PROCESSES FOR REFINING A REGISTERED MAP OF A BODY CAVITY;" the disclosures of which are hereby expressly incorporated herein by reference.

According to embodiments, various components of the mapping system 100, illustrated in FIG. 1, and/or the processing unit 200, illustrated in FIG. 2, may be implemented on one or more computing devices. A computing device may include any type of computing device suitable for implementing embodiments of the disclosure. Examples of computing devices include specialized computing devices or general-purpose computing devices such "workstations," "servers," "laptops," "desktops," "tablet computers," "handheld devices," "general-purpose graphics processing units (GPGPUs)," and the like, all of which are contemplated within the scope of FIGS. 1 and 2 with reference to various components of the system 100 and/or processing unit 200.

In embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in embodiments, the computing device may include a number of processors, a number of memory components, a number of I/O ports, a number of I/O components, and/or a number of power supplies. Additionally any number of these components, or combinations thereof, may be distributed and/or duplicated across a number of computing devices.

In embodiments, memory (e.g., the storage device 160 depicted in FIG. 1, and/or the memory 204 depicted in FIG. 2) includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 160 and/or 204 stores computer-executable instructions for causing a processor (e.g., the processing unit 120 depicted in FIG. 1 and/or the processor 202 depicted in FIG. 2) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Examples of such program components include the annotation waveform 206, the annotation histogram 208, the map 210, the acceptor 212, the annotation waveform generator 214, the histogram generator 216, the EGM classifier 218, and the mapping engine 220. Program components may be programmed using any number of different programming environments, including various languages, development kits, frameworks, and/or the like. Some or all of the functionality contemplated herein may also, or alternatively, be implemented in hardware and/or firmware.

Figure 3:
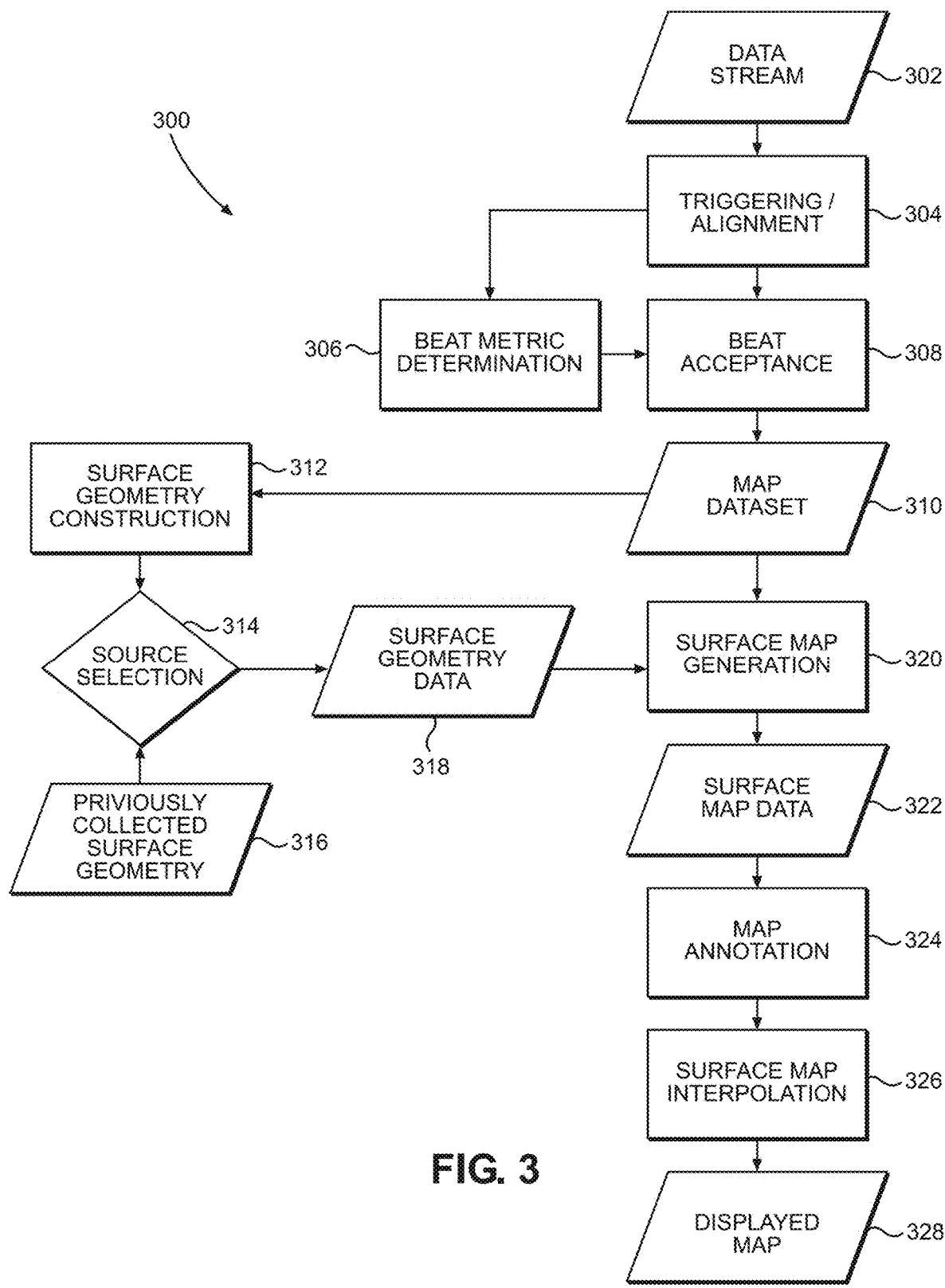
FIG. 3 is a flow diagram depicting an illustrative process for generating a cardiac map, in accordance with embodiments of the subject matter disclosed herein.

FIG. 3 is a flow diagram of an illustrative process 300 for automated electro-anatomical mapping, in accordance with embodiments of the disclosure. Aspects of embodiments of the method 300 may be performed, for example, by a processing unit (e.g., the processing unit 120 depicted in FIG. 1, and/or the processing unit 200 depicted in FIG. 2). A data stream 302 containing multiple signals is first input into the system (e.g., the cardiac mapping system 100 depicted in FIG. 1). During the automated electro-anatomical mapping process, a data stream 302 provides a collection of physiological and non-physiological signals that serve as inputs to the mapping process. The signals may be collected directly by the mapping system, and/or obtained from another system using an analog or digital interface. The data stream 302 may include signals such as unipolar and/or bipolar intracardiac electrograms (EGMs), surface electrocardiograms (ECGs), electrode location information originating from one or more of a variety of methodologies (magnetic, impedance, ultrasound, real time MRI, etc.), tissue proximity information, catheter force and/or contact information obtained from one or more of a variety of methodologies (force spring sensing, piezo-electric sensing, optical sensing etc.), catheter tip and/or tissue temperature, acoustic information, catheter electrical coupling information, catheter deployment shape information, electrode properties, respiration phase, blood pressure, other physiological information, and/or the like.

For the generation of specific types of maps, one or more signals may be used as one or more references, during a triggering/alignment process 304, to trigger and align the data stream 302 relative to the cardiac, other biological cycle and/or an asynchronous system clock resulting in beat datasets. Additionally, for each incoming beat dataset, a number of beat metrics are computed during a beat metric determination process 306. Beat metrics may be computed using information from a single signal, spanning multiple signals within the same beat and/or from signals spanning multiple beats. The beat metrics provide multiple types of information on the quality of the specific beat dataset and/or likelihood that the beat data is good for inclusion in the map dataset. A beat acceptance process 308 aggregates the criteria and determines which beat datasets will make up the map dataset 310. The map dataset 310 may be stored in association with a 3D grid that is dynamically generated during data acquisition.

Surface geometry data may be generated concurrently during the same data acquisition process using identical and/or different triggering and/or beat acceptance metrics employing a surface geometry construction process 312. This process constructs surface geometry using data such as electrode locations and catheter shape contained in the data stream. Additionally, or alternatively, previously collected surface geometry 316 may be used as an input to surface geometry data 318. Such geometry may have been collected previously in the same procedure using a different map dataset, and/or using a different modality such as CT, MRI, ultrasound, rotational angiography, and/or the like, and registered to the catheter locating system. The system performs a source selection process 314, in which it selects the source of the surface geometry data and provides surface geometry data 318 to a surface map generation process 320. The surface map generation process 320 is employed to generate surface map data 322 from the map dataset 310 and surface geometry data 318.

The surface geometry construction algorithm generates the anatomical surface on which the electroanatomical map is displayed. Surface geometry can be constructed, for example, using aspects of a system as described U.S. patent application Ser. No. 12/437,794, entitled "Impedance Based Anatomy Generation" and filed on May 8, 2008; and/or U.S. Pat. No. 8,948,837, entitled "Electroanatomical Mapping" and issued on Feb. 3, 2015, the contents of each of which is incorporated by reference herein in its entirety. Additionally, or alternatively, an anatomical shell can be constructed by the processing unit by fitting a surface on electrode locations that are determined either by the user or automatically to be on the surface of the chamber. In addition, a surface can be fit on the outermost electrode and/or catheter locations within the chamber.

As described, the map dataset 310 from which the surface is constructed can employ identical or different beat acceptance criteria from those used for electrical and other types of maps. The map dataset 310 for surface geometry construction can be collected concurrently with electrical data or separately. Surface geometry can be represented as a mesh containing a collection of vertices (points) and the connectivity between them (e.g. triangles). Alternatively, surface geometry can be represented by different functions such as higher order meshes, non-uniform rational basis splines (NURBS), and/or curvilinear shapes.

The generation process 320 generates surface map data 322. The surface map data 322 may provide information on cardiac electrical excitation, cardiac motion, tissue proximity information, tissue impedance information, force information, and/or any other collected information desirable to the clinician. The combination of map dataset 310 and surface geometry data 318 allows for surface map generation. The surface map is a collection of values or waveforms (e.g., EGMs) on the surface of the chamber of interest, whereas the map dataset can contain data that is not on the cardiac surface. One approach for processing the map dataset 310 and surface geometry data 318 to obtain a surface map dataset 322 is described in U.S. Pat. No. 7,515,954, entitled "NON-CONTACT CARDIAC MAPPING, INCLUDING MOVING CATHETER AND MULTI-BEAT INTEGRATION" and filed Jun. 13, 2006, the contents of which is incorporated by reference herein in its entirety.

Alternatively, or in combination with the method above, an algorithm that applies acceptance criteria to individual electrodes can be employed. For example, electrode locations exceeding a set distance (e.g., 3 mm) from surface geometry can be rejected. Another algorithm can incorporate tissue proximity information using impedance for inclusion in the surface map data. In this case only electrode location whose proximity value is less than 3 mm might be included. Additional metrics of the underlying data can also be used for this purpose. For example, EGM properties similar to beat metrics can be assessed on a per electrode basis. In this case metrics such as far field overlap and/or EGM consistency can be used. It should be understood that variations on the method to project points from the map dataset 310 to the surface and/or to select appropriate points can exist.

Once obtained, the surface map data 322 may be further processed to annotate desired features from the underlying data, a process defined as surface map annotation 324. Once data is collected into surface map data 322, attributes relating to the collected data may be automatically presented to the user. These attributes can be automatically determined and applied to the data by the computer system and are referred to herein as annotations. Exemplary annotations include activation time, the presence of double activation or fractionation, voltage amplitude, spectral content, and/or the like. Due to the abundance of data available in automated mapping (e.g., mapping completed by the computer system with minimal human input related to the incoming data), it is not practical for the operator to review and annotate data manually. However, human input can be a valuable addition to the data, and so when user input is provided it is necessary for the computer system to automatically propagate and apply it to more than one data point at a time.

It may be possible to use the computer system to automatically annotate activation time, voltage, and other characteristics of individual EGMs. Activation time detection may use methods similar to those previously described to detect a trigger and can similarly benefit from the use of blanking and powered triggering operator. Desired annotations may include instantaneous potential, activation time, voltage amplitude, dominant frequency and/or other properties of the signal. Once computed, the annotations may be displayed superimposed on chamber geometry. In embodiments, a gap-filling surface map interpolation may be employed 326. For example, in embodiments, a gap-filling interpolation may be employed where a distance between a point on the surface to a measured EGM exceeds a threshold, as this may indicate, for example, that grid-based interpolation, as described herein, may not be as effective in that situation. Displayed maps 328 can be computed and displayed separately, and/or overlaid on top of each other.

The illustrative process 300 shown in FIG. 3 is not intended to suggest any limitation as to the scope of use or functionality of embodiments of the present disclosure. Neither should the illustrative process 300 be interpreted as having any dependency or requirement related to any single component or combination of components illustrated therein. Additionally, any one or more of the components depicted in FIG. 3 may be, in embodiments, integrated with various ones of the other components depicted therein (and/or components not illustrated), all of which are considered to be within the ambit of the present disclosure.

Figure 4:
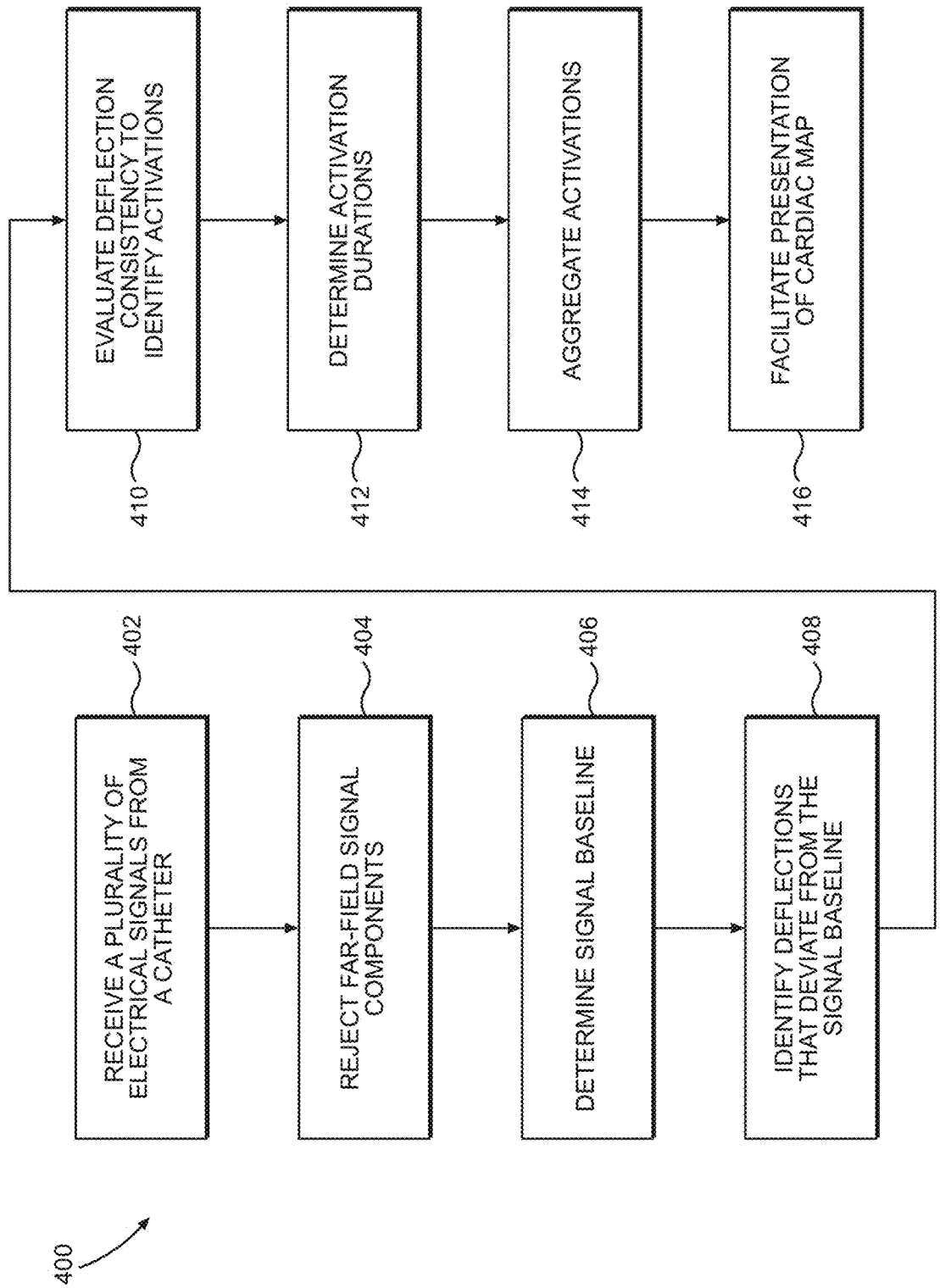
FIG. 4 is a flow diagram depicting an illustrative method of processing electrophysiological information, in accordance with embodiments of the subject matter disclosed herein.

FIG. 4 is a flow diagram depicting an illustrative method 400 of processing electrophysiological information, in accordance with embodiments of the disclosure. Aspects of embodiments of the method 400 may be performed, for example, by a processing unit (e.g., the processing unit 120 depicted in FIG. 1, and/or the processing unit 200 depicted in FIG. 2). Embodiments of the method 400 include receiving a plurality of electrical signals from a catheter (block 402). The catheter may be any catheter having one or more electrodes configured to obtain electrical signals (e.g., the mapping catheter 110 depicted in FIG. 1, a CS catheter, an ablation catheter, etc.). The processing unit also may receive an indication of a measurement location corresponding to each of the electrical signals. As explained above, with respect to FIG. 3, the processing unit and/or other components (e.g., the electrical module 140 depicted in FIG. 1) may be configured to determine whether to accept particular electrical signals (e.g., beats) based on one or more beat acceptance criteria.

According to embodiments, cardiac electric signal features may be extracted from the cardiac electrical signals (e.g., EGMs). Examples of features of the cardiac electrical signals include, but are not limited to, activation times, minimum voltage values, maximum voltages values, maximum negative time-derivatives of voltages, instantaneous potentials, voltage amplitudes, dominant frequencies, peak-to-peak voltages, and/or the like. Each of the respective points at which a cardiac electrical signal is sensed may have a corresponding set of three-dimensional position coordinates. For example, the position coordinates of the points may be represented in Cartesian coordinates. Other coordinate systems can be used, as well. In embodiments, an arbitrary origin is used and the respective position coordinates are defined with respect to the arbitrary origin. In some embodiments, the points have non-uniform spacing, while in other embodiments, the points have uniform spacing. In embodiments, the point corresponding to each sensed cardiac electrical signal may be located on the endocardial surface of the heart and/or below the endocardial surface of the heart.

Figure 5A:
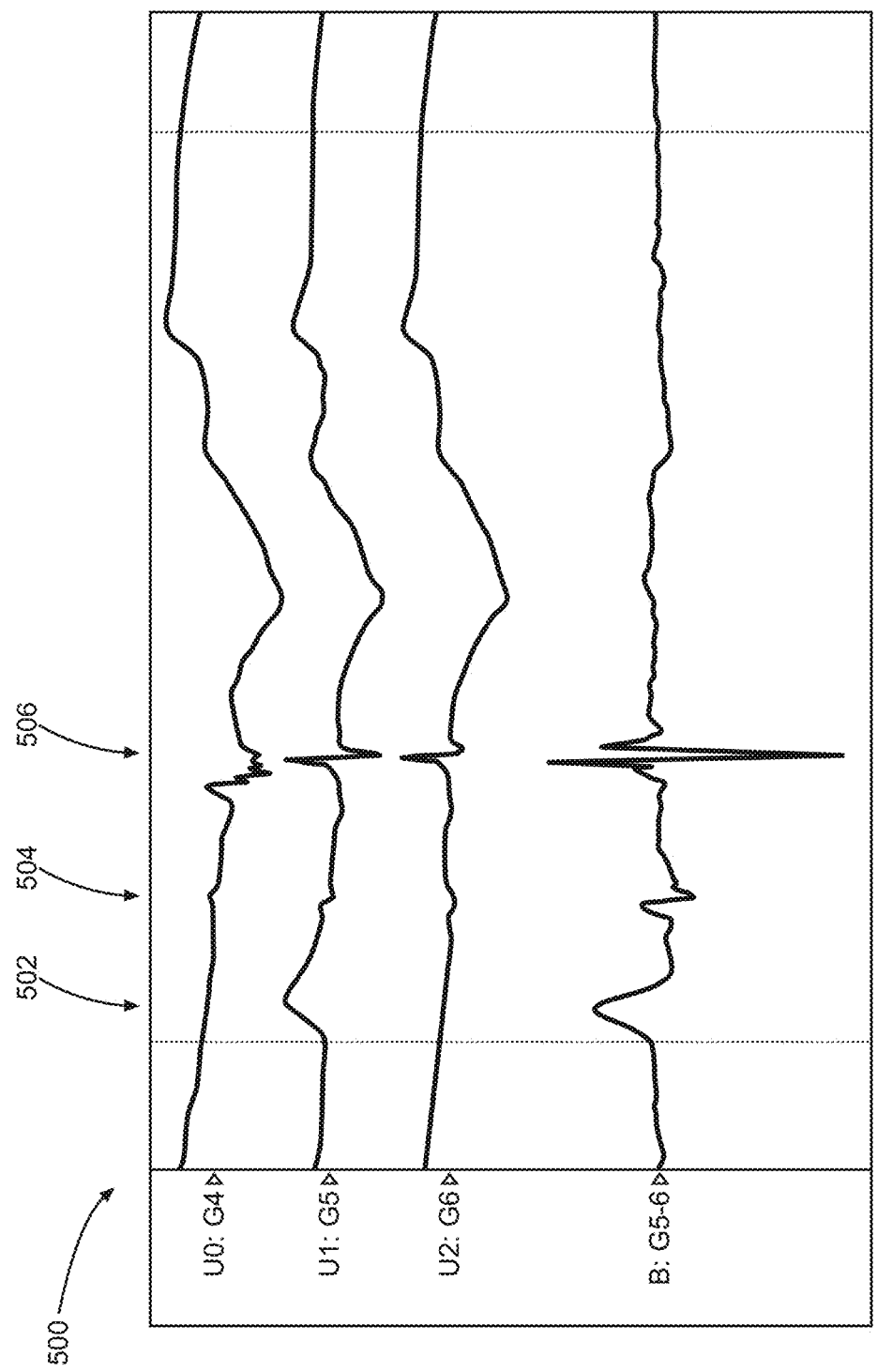
FIG. 5A depicts an illustrative graphical representation of electrical signals received from a mapping catheter, in accordance with embodiments of the subject matter disclosed herein.

FIG. 5A shows an exemplary graphical representation 500 illustrating electrical signals (in this case, EGMs) received from a mapping catheter, each representing a magnitude of a depolarization sequence of a heart during a predetermined time period. In this example, a first signal U0 may be associated with a first electrode G4, a second signal U1 may be associated with a second electrode G5, and a third signal U2 may be associated with a third electrode G6. The signals U0, U1, U2 may represent unipolar signals received from a first mapping catheter and a fourth signal B may represent a bipolar signal associated with the second and third electrodes G5 and G6. In embodiments, the bipolar signal B may represent a graphical summation of signals received from the second and third electrodes G5 and G6. In embodiments, and, for example, depending on a lead tip configuration of a catheter, the acquired electrical signals may be unipolar signals, bipolar signals, and/or other multipolar signals.

With continuing reference to FIG. 4, to filter out unwanted signals, embodiments of the method 400 also include rejecting or attenuating far-field signal components from the acquired electrical signals (block 404). For example, R-waves sensed by an atrial channel of the heart that are unrelated to the diagnostic assessment may be rejected or attenuated as unwanted signals. Other exemplary unwanted signals may include common mode noise such as power-line noise, T-waves, skeletal muscle myopotentials (e.g., from a pectoral muscle), and crosstalk signals from another device (e.g., a pacemaker) to suit different applications. In embodiments, far-field signal components may be rejected or attenuated by creating a multipolar signal (e.g., the bipolar signal B associated with the second and third electrodes G5 and G6, depicted in FIG. 5A, a tripolar signal, etc.). Any number of other techniques may be implemented for processing the electrical signals such as, for example, signal conditioning, filtering, transforming, and/or the like. In embodiments, the method 400 may include any number of other types of artifact rejection. For example, in embodiments, artifact rejection may be achieved using spatio-temporal analysis (e.g., as described below with reference to block 410), morphological analysis, continuous-mode artifact rejection, (e.g., unipolar rejection), combinations of unipolar and/or multipolar signals (e.g., nonlinear combination of all received signals), and/or the like. Any number of other types of filtering may be performed on the electrical signals. As such, for example, the term electrical signal may also include filtered electrical signals (e.g., as used in connection with subsequent processing steps).

Embodiments of the method 400 include identifying far-field signal components, but not necessarily rejecting or attenuating the identified far-field signal components. In embodiments, for example, far-field signal components may include information that can be used for various aspects of analyses of cardiac electrical signals. For example, far-field signal components may include information about neighboring anatomical structures. Far-field signal components may be identified, isolated, analyzed, and/or the like. In embodiments, the method 400 may include identifying far-field signal components, and taking some action in response thereto. That is, for example, in embodiments, far-field signal components may be used in conjunction with detection of local, spatially-varying activation for identifying tachycardia-sustaining isthmus, and/or the like.

Embodiments of the method 400 further include determining a signal baseline (block 406) during a quiescent time period. The signal baseline, which may be determined based on historical information, population information, patient information, environmental information, and/or the like, may include a value or range of values determined such that deflections of the EGM deviating beyond the baseline by a specified amount are deemed to be activations. The signal baseline may be generic, patient-specific, EGM-specific, time-varying, and/or the like. In embodiments, the signal baseline may be a pre-determined minimum value and/or maximum value.

In embodiments, a signal baseline may be determined such that deflections deviating beyond the signal baseline have some computed probability (or minimum probability) of being activations. According to embodiments, the signal baseline may include a range of values that represent, and/or are determined based on a noise floor. That is, for example, a noise floor may be estimated and the signal baseline established as the upper and lower boundaries of the noise floor, a multiple of the noise floor, and/or some other function of the noise floor (e.g., within a certain standard deviation of the noise floor, etc.). According to embodiments, for example, a signal baseline determination process may include identifying "quiet periods" within a specified window (e.g., a 0.5 second time window, a 1 second time window, etc.), and determining the signal baseline based on the quiet periods. That is, for example, within a specified window, one or more time periods may be identified in which the amplitude of the electrical signal is within a specified range, and/or within a specified distance from other amplitudes. An electrical signal may be an electrogram (EGM), a filtered EGM, a set of absolute values of an EGM, values of peaks of an EGM at peak locations, a combination of these, and/or the like. For example, an electrical signal may be represented as a set of ordered values (e.g., the amplitude of each sample point may be a value in the set), and a specified percentile and/or multiplier thereof, may be used to define the signal baseline. That is, for example, a multiplier of the $20^{th}$ percentile (e.g., the $20^{th}$ lowest value or bin of values) may be used to define the signal baseline. In embodiments, to determine the signal baseline, one or more electrical signals may be dilated, and the dilated electrical signal (e.g., dilated EGM) may be used to compute the $20^{th}$ percentile. Dilation is an operation that replaces every sample with the maximum of the samples in a specified time window (e.g., 15 ms, 20 ms, 25 ms, etc.). Dilation can also be described, for example, as a moving maximum (similar to a moving average, but in which values are replaced with the maximum value in the window instead of the average value). Similar analyses may be implemented with regard to any one or more other characteristics of an electrical signal (e.g., frequency, signal-to-noise ratio (SNR), etc.), and/or the like.

In embodiments, the signal baseline may be determined based on particular attributes of a specific patient, environmental information, corresponding portions of a cardiac cycle, aspects of a reference signal, and/or the like. Additionally, or alternatively, the signal baseline may be determined based on a certain sample of information such as, for example, information associated with a set of acquired EGMs within a specified region. The specified region also may be used to identify the EGMs used in any number of other aspects of embodiments of the method 400. The specified region may be defined (e.g., in one dimension (1D), two dimensions (2D), three dimensions (3D), etc.) according to a specified radius. In embodiments, the specified radius may be, be similar to, include, be included within, and/or be determined based on, a stochastic radius such as is described in U.S. application Ser. No. 15/230,233, entitled "CARDIAC MAPPING USING A 3D GRID," filed on Aug. 5, 2016, and which claims the priority benefit of U.S. Provisional Application No. 62/202,711, having the same title, and filed on Aug. 7, 2015, the entirety of each of which is hereby expressly incorporated herein by reference for all purposes.

In embodiments, the specified region may be defined in the context of time such as, for example, by defining the specified region to be the spatial region that includes any EGMs recorded during a specified time period (e.g., during the window of analysis). Any number of different combinations of the above characteristics of the specified region may be implemented and may include any number of other considerations (e.g., a specified arrhythmia, a specified treatment, a specified medical device, etc.).

In embodiments, the specified region may be predetermined and/or fixed. In embodiments, the specified region may be determined by calculating a maximum distance between two adjacent points on a grid or graph used for aggregating acquired electrical signals, and/or may be configured to optimize the relevance of aggregate values from the grid and/or graph that may be interpolated onto an anatomical mesh, aggregate activation information associated with activation waveforms, and/or the like. The specified region may be defined using any number of different measurements of distance (e.g., a rectilinear distance, L1, a Euclidean distance, L2, etc.), time, relevance (e.g., confidence levels, weightings, etc.).

The specified region may be adaptive and may be dynamically adjusted based on any number of different factors such as, for example, user input, mapping quality metrics (e.g., a surface projection distance (SPD), which is the maximum distance that an electrode can fall from a mesh surface and still be projected into the map, which may be set and/or adjusted to facilitate control over the accuracy of the map), environmental parameters, physiological parameters, and/or the like.

As is further shown in FIG. 4, embodiments of the method 400 include identifying one or more deflections in an electrical signal that deviate beyond the signal baseline according to one or more specified criteria (block 408). For example, a deflection may be identified wherein the amplitude of the signal exceeds a signal baseline value, wherein the amplitude of the signal deviates beyond baseline by a specified amount (e.g., a relative deviation), and/or the like. In this manner, while the identification of deflections deviating beyond the signal baseline according to one or more specified criteria may have a weak amplitude dependency, this identification is generally not dependent upon, or affected by, variations in amplitude within ranges based on the baseline signal.

In embodiments, identifying deflections that deviate beyond the signal baseline may include determining, for each sample point of an electrical signal, a corresponding activation waveform value. For example, in embodiments, the method 400 may include determining a probability (e.g., a value between 0 and 1, inclusive) that a given sample point represents an activation, based on its relation to the signal baseline. In embodiments, other numerical scales may be used for assigning the probability such as, for example, values between 0 and 100, and/or the like. In embodiments, a likelihood (e.g., a probability) that a signal deflection represents an activation may be determined based on the deviation of that deflection from the signal baseline. For example, a deflection having a maximum amplitude that deviates from the signal baseline by at least a specified amount may be assigned a probability of 1, while a deflection having a maximum amplitude that deviates from the signal baseline by at most a specified amount may be assigned a probability of 0. Probabilities may be assigned, in linear and/or nonlinear, fashions to deflections having amplitudes that are not satisfied by either of the preceding criteria based on, for example, the relative deviation of the deflection amplitude with respect to the above criteria. In this manner, for example, an activation waveform value may be a probability that an identified deflection corresponding to a sample point represents an activation.

According to embodiments, original EGM information during detected periods of deviation from baseline may be used to further refine the likelihood of activation. This information may include, for example, the slope of the EGM, the monotonicity of the EGM (e.g., whether the slope stays positive for 1 ms or for 40 ms before becoming negative), the presence of adjacent deflections, and/or the like. In embodiments, for example, detected baseline deviations having a slope close to 0 (e.g., within a specified range around 0) may have their likelihood score diminished. Detected baseline deviations that contain a monotonic EGM signal (e.g., the slope does not change sign) for specified time durations (e.g., for greater than 11 ms) may have their likelihood score diminished. In embodiments, detected deviations from baseline that are adjacent or overlapping other deviations from baseline with larger amplitude may have their likelihood score diminished. This may be done by comparing the prominence of the peak of a deflection to the prominence of the adjacent peaks and diminishing the likelihood score as this ratio falls. A deflection that fits this description can be visually described as a shoulder of a larger amplitude deflection.

In embodiments, for example, activation waveform values may represent confidence levels associated with each sample point. That is, for example, an activation waveform value of 1, or approximately 1, may indicate a relatively high (e.g., relative to confidence levels associated with other values between 0 and 1) level of confidence that the corresponding sample point represents a deflection from the signal baseline due to an activation, while an activation waveform value of 0, or approximately 0, may indicate a relatively low (e.g., relative to confidence levels associated with other values between 0 and 1) level of confidence that the corresponding sample point represents a deflection from the signal baseline due to an activation. In embodiments, the activation waveform values may be determined using any number of different statistical models, physiological models, and/or the like. According to embodiments, the calculations (e.g., models, formulas, etc.) used to determine activation waveform values may be configured to minimize dependency on amplitude. In embodiments, the calculations used to determine activation waveform values may be biased toward generating activation waveform values that are either close to (e.g., approximately) 0 or close to 1. For example, weightings, step-wise functions, discrete transforms, and/or the like may be used to bias the determination of each activation waveform value toward 0 or 1. In this manner, a plurality of sample points of an electrical signal may be represented by a plurality of activation waveform values that form an activation waveform that has an approximately discrete distribution, thereby facilitating the efficient identification of activations, even in the case of fractionated EGMs. Accordingly, embodiments may facilitate detecting activations, which may facilitate more accurate and efficient mapping, ablating, and/or the like.

In embodiments, an activation waveform value may be determined and/or further adjusted based on further analysis such as, for example, results of a consistency evaluation, as described below with reference to block 410. Any number of other types of information and/or analyses may be incorporated to refine determination of activation waveform values for each sample point of an electrical signal. In embodiments, one or more machine-learning techniques (e.g., supervised and/or unsupervised classifiers, neural networks, deep learning, artificial reasoning, etc.) may be used to modify aspects of embodiments of the method 400 such as, for example, by enhancing (e.g., making more efficient, accurate, etc.) an activation waveform value calculation formula, and/or the like.

Figure 5B:
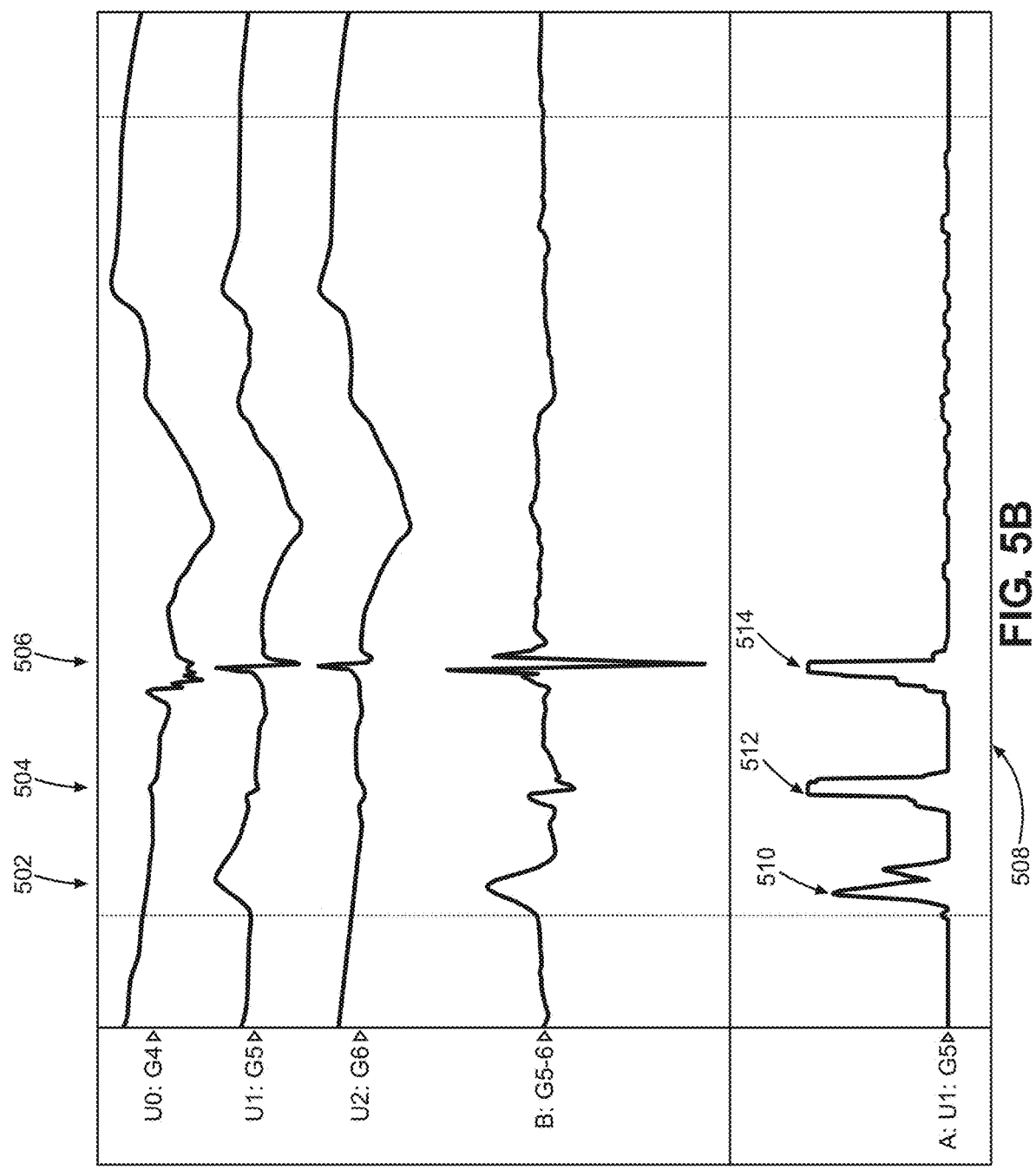
FIG. 5B depicts an activation waveform corresponding to the illustrative graphical representation of electrical signals depicted in FIG. 5A, in accordance with embodiments of the subject matter disclosed herein.

According to embodiments, identification of deflections from the baseline signal according to specified criteria may include identification of potential activations, which may be represented, for example, using an activation waveform (e.g., the annotation waveform 206 depicted in FIG. 2). For example, FIG. 5B shows an exemplary graphical representation 508 of an activation waveform A having activations 510, 512, 514, all activations detected from the electrical signal U1 received from the electrode G5 during the predetermined time period. In embodiments, the activation waveform represents identification of activations based on absolute values of deflections that deviate beyond a baseline signal according to one or more specified criteria (e.g., having an absolute value of a maximum amplitude greater than or equal to a threshold value).

As shown in FIG. 5B, a first activation 510 corresponds to a first deflection 502 detected in the signal U1, a second activation 512 corresponds to a second deflection 504 detected in the signal U1, and a third activation 514 corresponds to a third deflection 506 detected in the signal U1. As shown in FIG. 5A, the electrical signals U0, U1, U2 may be evaluated during a predetermined time period for the diagnostic assessment. As an example only, an electrical signal having multiple myocardial capture signals, each having a predetermined amplitude and a predetermined pulse width, may be evaluated to detect activations during the predetermined time period. In embodiments, the amplitude of each activation represented on the graphical representation of the activation waveform may correspond to a specified value (e.g., each activation may be assigned an amplitude of 1), an amplitude (e.g., voltage, current density, etc.) of one or more electrical signals associated with the identified activation, an aggregated amplitude value corresponding to one or more electrical signals associated with the identified activation (e.g., a mean amplitude, a median amplitude, etc.), and/or the like. In embodiments, each activation may represent a bin of an activation histogram, and the amplitude of the activation in the activation histogram may represent a relative population of the associated bin (e.g., relative to the population of one or more other bins). An activation histogram is a histogram constructed from one or more activation waveforms. Similarly, an annotation histogram is a histogram constructed from one or more annotation waveforms.

In embodiments, noise and artifact signals (e.g., deflection 502 in signal U1) may still be included in the waveform A. To remove the noise and/or artifacts, thereby creating a filtered activation waveform A, embodiments of the method 400 include performing an artifact rejection against the activation waveform based on a spatiotemporal deflection consistency between two or more electrical signals (block 410). According to embodiments, consistency may be determined in any number of different ways. For example, spatiotemporal deflection consistency between two electrical signals may refer to the occurrence of corresponding identified deflections at approximately the same time, within a specified time window, and/or the like. In embodiments, for example, a deflection that occurs in less than all of a specified set of electrical signals may be rejected as being an artifact. In embodiments, only deflections that are identified as deviating from a signal baseline according to one or more criteria are used in the consistency determination. In this manner, for example, although a first unipolar EGM may include a deflection that corresponds to a deflection identified in another EGM, the deflections may be considered to be inconsistent if the first deflection does not deviate beyond the signal baseline according to one or more signal criteria. According to embodiments, the step of evaluating deflection consistency to identify activations depicted in block 410 may be, include, be similar to, be included in, or be otherwise integrated with the step of rejecting far-field signal components depicted in block 404.

Embodiments of the artifact rejection processes described above may utilize a map and/or a grid that holds beat-gated data collected during the same rhythm. The location of the various collected signals may be used to decide whether the information in these signals should be used for artifact rejection. In embodiments, the artifact rejection may be accomplished using techniques similar to those discussed below regarding "continuous" artifact rejection. In embodiments, in contrast to the "continuous" artifact rejection, the methods discussed above may include comparing a first signal to at least a second signal that was collected at a different time than the time during which the first signal was collected. In embodiments, this may include establishing assumptions such as, for example, that the data used for artifact rejection was collected during the same rhythm, that the data used for artifact rejection was collected at the same phase of the cardiac cycle, and/or the like.

According to embodiments, a "continuous" method of assessing spatiotemporal deflection consistency to detect artifacts may be used. In embodiments of a continuous method, deviations from a baseline signals may be detected for various combinations of EGMs on a catheter (e.g., all combinations of bipolar and tripolar signals on a channel such as, e.g., tripolar signal G4-G5-G6, bipolar signal G4-G5, bipolar signal G5-G6, bipolar signal G4-G6, etc.). These baseline deviation signals may be used together to determine whether the observed deviation on any one signal is an activation or an artifact. In embodiments, this continuous method may be configured as a majority rule or voting process. In embodiments, the method may be configured as a minimum operation between the different baseline deviation signals. In embodiments, this kind of "continuous" artifact rejection compares simultaneously collected data. It does not require a cardiac map. The locations of the signals may be determined from the location relationship of the physical electrodes on the catheter.

Activations having inconsistent deflections may be removed or reduced from the activation waveform. In this way, only consistent deflections may remain in the activation waveform for examination, thereby reducing the manual examination time and costs, while facilitating the removal of noise and/or artifacts. In embodiments, for example, the plurality of electrical signals, such as the first, second, and third signals U0, U1, U2, are compared to one another and/or the activation waveform A for detecting one or more consistent deflections that are within a range of predetermined limits (e.g., minimum and maximum thresholds) relative to the signal baseline.

Figure 5C:
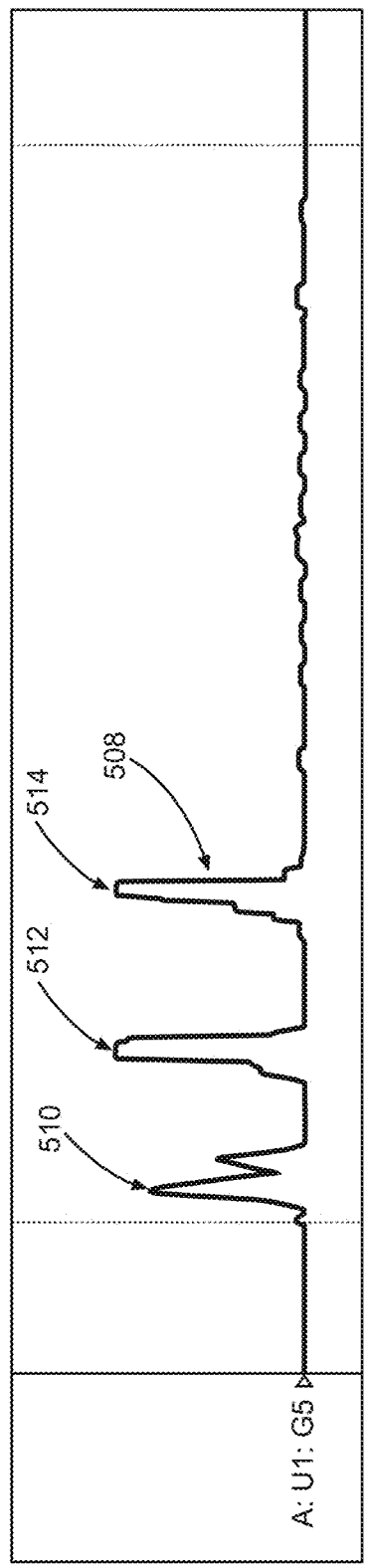
FIG. 5C depicts an illustrative graphical representation of the activation waveform depicted in FIG. 5B, in accordance with embodiments of the subject matter disclosed herein.
Figure 5D:
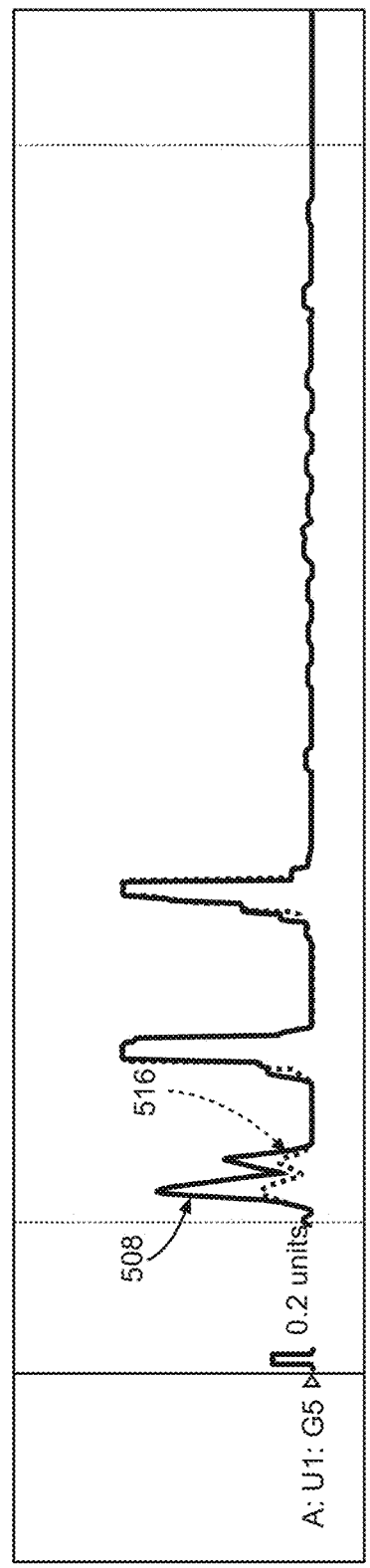
FIG. 5D depicts an illustrative graphical representation of a filtered activation waveform based on the activation waveform depicted in FIGS. 5B and 5C, in accordance with embodiments of the subject matter disclosed herein.

FIGS. 5C and 5D show the graphical representation 508 of the activation waveform A, and an illustrative graphical representation 516 of a filtered activation waveform A, having activations with only consistent deflections. In FIG. 5D, the graphical representation 516 is overlaid on top of the graphical representation 508 for easy comparison. For example, in the graphical representation 516, the first activation 510 is virtually eliminated due to inconsistency demonstrated in the signal U1. More specifically, as shown in FIG. 5, the deflection 502 of the signal U1 is inconsistent with and does not appear in other neighboring signals U0 and U2. Thus, the first activation 510 is effectively eliminated from the filtered activation waveform A. In contrast, as shown in FIG. 5, the defections 504 and 506 of the signal U1 are consistent with the deflections 504 and 506 of the neighboring signals U0 and U2. Hence, in FIG. 5D, a second activation 512 corresponding to the defection 504 and a third activation 514 corresponding to the deflection 506 remain in the filtered activation waveform A. Due to the removal of activations with inconsistent deflections, an accuracy of a cardiac map may be greatly improved.

Embodiments of the method 400 also include determining one or more activation durations (block 412), which may represent a length of an activation. That is, for example, an EGM may include a portion thereof for which all of the amplitudes deviate beyond the signal baseline according to the specified criteria. The length of the time period corresponding to that portion of the EGM may be identified as an activation duration. In embodiments, the activation waveform may be represented along a time scale, in which case, the waveform may represent the activation duration. For example, the width of the deflection in the activation waveform may represent the duration of the corresponding activation.

Embodiments of the method 400 further include aggregating the detected activations (block 414) such as, for example, by generating one or more activation waveforms, activation histograms, and/or the like. The activation waveforms and/or activation histograms may be used in facilitating presentation of the cardiac map (block 416). For example, embodiments may include annotating an electroanatomical map (e.g., a cardiac map) based on one or more annotation waveforms, annotation histograms, and/or the like. Additionally, or alternatively, the annotation waveforms and/or annotation histograms may be used in facilitating other processes such as, for example, ablation, recording information, diagnosis, and/or the like. That is, for example, in embodiments, annotation waveforms and/or annotation histograms may be used in the creation of a cardiac map (e.g., as part of a beat acceptance step such as, e.g., the beat acceptance step 308 depicted in FIG. 3), the annotation of a cardiac map (e.g., to annotate activation times), the display of a cardiac map (e.g., to facilitate a display of the spatial and/or temporal distribution of activation times), the augmenting of information (e.g., to facilitate determining and/or highlighting (e.g., emphasizing computationally and/or visually) characteristics of EGMs (which may be displayed) and/or EGMs having certain characteristics), an ablation procedure (e.g., to detect activations, distinguish between activations and artifacts, etc.), and/or the like. For example, in embodiments, annotation waveforms and/or annotation histograms may be used to facilitate quantification of specific EGM characteristics (e.g., by using activation waveforms to determine metrics such as, e.g., a portion of time during which a channel was active (activation duration), etc.).

In embodiments, a cardiac map may be generated and/or annotated based, at least in part, on the cardiac electrical signal features and/or the activation waveform (which may also be a cardiac electrical signal feature). In embodiments, the cardiac map may also be generated and/or annotated, at least in part, using any number of other signals, techniques, and/or the like. For example, embodiments may utilize impedance mapping techniques to generate and/or annotate one or more portions of the cardiac map such as, for example, an anatomical shell upon which electrical signal features are represented. In embodiments, a surface may be fitted on one or more of the points associated with the cardiac electrical signals to generate a shell representing the endocardial surface of the one or more cardiac structures. In embodiments, a surface may also be fitted on one or more of the points associated with the cardiac electrical signals to generate a shell representing an epicardium surface or other excitable cardiac tissue. In embodiments, one or more of the cardiac electrical signal features at the corresponding points can be included on the shell to generate a cardiac map of the one or more cardiac structures. For example, embodiments may include displaying annotations on the cardiac map that represent features, extracted from the cardiac electrical signals and/or derived from other features, such as, for example, activation times, minimum voltage values, maximum voltages values, maximum negative time-derivatives of voltages, instantaneous potentials, voltage amplitudes, dominant frequencies, peak-to-peak voltages, and/or the like.

Cardiac electrical signal features may be represented on the cardiac map and may be, or include, any features extracted from one or more corresponding sensed cardiac electrical signals and/or derived from one or more of such features. For example, a cardiac electrical signal feature may be represented by a color, such that if the cardiac electrical signal feature has an amplitude or other value within a first range then the cardiac electrical signal feature may be represented by a first color, whereas if the cardiac electrical signal feature has an amplitude or other value that is within a second range that is different than the first range, the cardiac electrical may be represented by a second color. As another example, the cardiac electrical signal feature may be represented by a number (e.g., a 0.2 mV sensed cardiac electrical signal feature can be represented by a 0.2 at its respective position on the surface map). Examples of a cardiac electrical signal feature that can be represented at the first surface point include, but are not limited to, an activation, an activation time, an activation duration, an activation waveform, a filtered activation waveform, an activation waveform characteristic, a filtered activation waveform characteristic, a minimum voltage value, a maximum voltages value, a maximum negative time-derivative of voltage, an instantaneous potential, a voltage amplitude, a dominant frequency, a peak-to-peak voltage, and/or the like.

In embodiments, other features such as, for example, non-electrical signal features, non-cardiac electrical signal features, and/or the like, can be represented on an anatomical map at respective locations. Examples of non-electrical signal features include, but are not limited to, features derived from magnetic resonance imaging, a computerized tomography scan, ultrasonic imaging, and/or the like.

According to embodiments, activation waveforms, as described above, may be useful for facilitating any number of different functionalities. For example, in embodiments, activation waveforms may be used to generate activation maps that more clearly represent activation propagation. In embodiments, activation waveforms may facilitate automatic classification of electrical signals such as EGMs. Activation waveforms may be used to facilitate cardiac mapping tools such as, for example, tools that facilitate accurate interpretation of activation maps. For example, embodiments facilitate generating activation histograms representing classifications associated with amounts of tissue activating at each activation time within a specified time period. Activation histogram waveforms may be presented on a display device, and may be associated with a cardiac map. Activation histogram waveforms may facilitate identifying and focusing on certain cardiac events, small tissue regions with activation times satisfying a certain set of criteria, and/or the like. Similarly, local activation histograms may facilitate map interpretation and navigation by representing aggregated activity across smaller regions of tissue.

Activation Waveform Propagation

According to embodiments, an activation waveform may be used (e.g., by a processing unit such as the processing unit 120 depicted in FIG. 1 and/or the processing unit 200 depicted in FIG. 2) to facilitate producing a dynamic region-of-interest mask that represents at least a portion of the activation waveform (e.g., in a static representation), and/or that represents the activation waveform over a changing time duration (e.g., in a dynamic representation). In embodiments, for example, a static representation may include a cardiac map having annotation information represented by one or more colors, the at least a portion of the activation waveform being represented by a highlighted portion of the annotation information, and the dynamic representation may include the cardiac map on which the highlighted portion changes as time progresses. The time duration may be swept over a mapping window to create an animation that shows a propagation map of significant potentials for each EGM. According to embodiments, the activation waveform propagation map may be more readable than traditional propagation maps that show only one selected potential for each EGM.

An activation waveform propagation map that represents events of interest may be created by sequentially highlighting map regions where EGMs are active during the specified time period, according to their respective activation waveforms. In this manner, activation waveform propagation maps may show patterns of activation while reducing, with respect to conventional systems, possibly incorrect annotations or reductionist assumptions associated with traditional propagation maps. In embodiments, an activation waveform propagation map may be generated using a number of activation waveforms, each activation waveform corresponding to one of the EGMs represented in the map.

Any number of different methods for highlighting activation regions may be employed in embodiments. For example, for a given time step or time period, the processing unit may be configured to identify activation regions of the map—that is, regions that include activation locations at which activations are identified during the time step/period. A region around the activation locations may be determined based on margins of error, statistical techniques for determining probabilities associated with activation occurrences, characteristics of the activation region at one or more previous time steps/periods, and/or the like. According to embodiments, a graphical user interface (GUI) used for presenting an activation waveform propagation map may include any number of different input tools for manipulating the map. For example, the GUI may include a play/pause button, a tool configured to facilitate manual selection of the time step, tools configured to facilitate manual adjustment of parameters (e.g., signal baseline definitions, thresholds, electrical signal characteristics, filters, etc.), and/or the like. In embodiments, for example, the GUI may include a selection tool that can facilitate refining selections of highlighted EGMs, select particular EGMs and/or activations, and/or the like.

For example, in embodiments, the GUI may include one or more selection tools configured to enable a user to make a temporal selection and/or a characteristic selection. That is, for example, embodiments may include presenting a selection tool on the GUI and, upon receiving a user input associated with the selection tool, highlighting corresponding portions of the cardiac map. For example, such a selection tool may enable a user to cause the processing unit to facilitate highlighting of surface areas of the cardiac map representing tissue that is activating during a certain time window. In embodiments, such a temporal selection may result in a static and/or dynamic representation of the selected information. According to embodiments, a characteristic selection tool may also be provided on the GUI, and the processing unit may be configured to receive user input via a user input device associated with the characteristic selection tool, where the user input includes a selection of one or more electrical signal characteristics (e.g., extracted features), activation waveform characteristics, and/or the like. In embodiments, such a characteristic selection tool may result in a static and/or dynamic representation of the selected information, though generally a static representation may be easier to understand. For example, in embodiments, a characteristic selection tool may enable a user to cause the processing unit to facilitate highlighting activations that have a certain characteristic (e.g., all activations that have an activation duration of at least 20 milliseconds, etc.). According to embodiments, the temporal and/or characteristic selection tools may include virtual sliders, knobs, cursors, and/or the like. In embodiments, a temporal and/or characteristic selection tool may facilitate selection of a selectable representation of a time period and a characteristic, respectively.

Figure 6A:
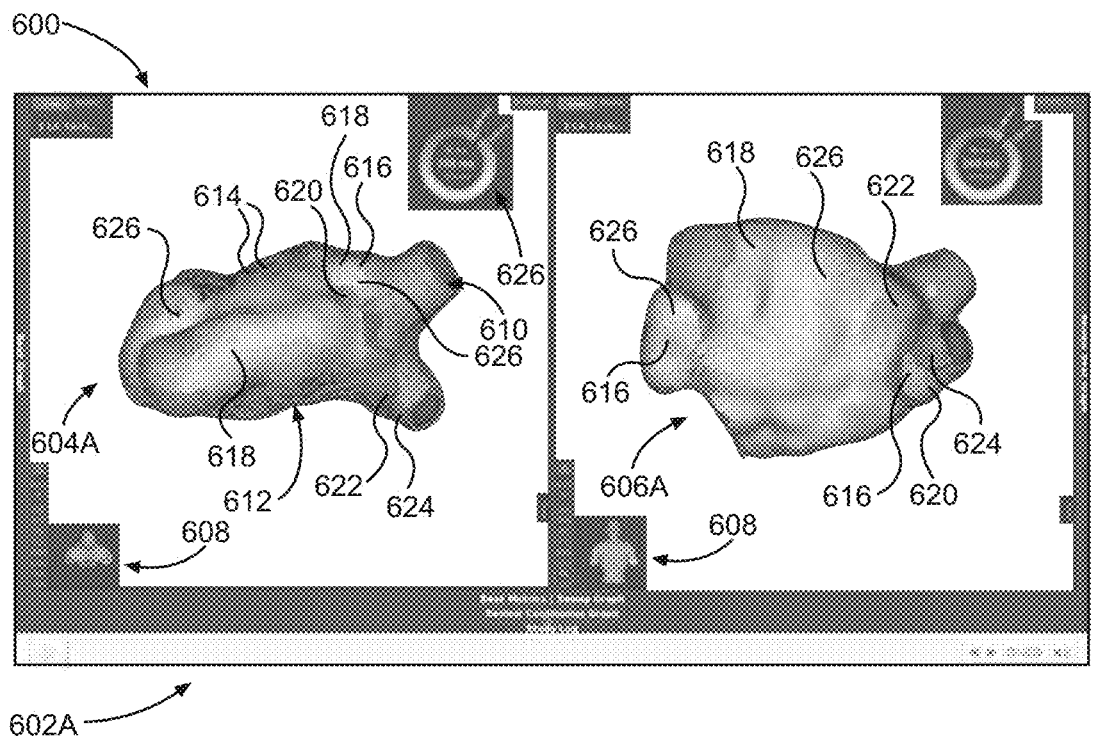
FIGS. 6A-6D depict instances of an illustrative graphical user interface (GUI) upon which is presented a conventional activation map, in accordance with embodiments of the subject matter disclosed herein.

FIGS. 6A-6D depict illustrative screenshots from an interactive graphical user interface (GUI) 600 presented using a display device associated with a cardiac mapping system, showing views of an illustrative cardiac map, in accordance with embodiments of the subject matter disclosed herein. According to embodiments, the cardiac mapping system may be, be similar to, include similar features as, include, or be included within the mapping system 100 depicted in FIG. 1. FIG. 6A depicts a first instance 602A of the GUI 600. The GUI 600 includes a first view 604A of the first instance 602A of the cardiac map and a second view 606A of the first instance 602A of the cardiac map. As used herein, an "instance" of an anatomical map (e.g., a cardiac map) refers to the anatomical map corresponding to a certain point in time. Thus, for example, a first instance of the cardiac map may present information associated with a first time and a second instance of the cardiac map may present information associated with a second time, the second time being later in time than the first time.

As shown, the first view 604A and the second view 606A represent two different orientations of the same cardiac map. In embodiments, the GUI 600 may be configured to present only one view of the cardiac map at a time. In embodiments, the GUI 600 may be configured to present, simultaneously, sequentially, and/or alternatively, any number of different views of any number of cardiac maps. In embodiments, for example, the GUI 600 may be configured to present a first cardiac map having annotations representing activations and a second cardiac map having annotations representing electrical potential, current density, and/or the like. As shown, an orientation indicator 608 may be configured to indicate the orientation, with respect to the body housing the heart, of the cardiac map that corresponds to the particular view 604A, 606A.

As shown in FIG. 6A, the cardiac map includes an anatomical shell 610 and annotations 612 displayed on the anatomical shell 610. In embodiments, the map may be an activation map, on which activation locations are indicated by raised bumps 614 and activation timing is represented using colors 616, 618, 620, 622, 624, and 626. That is, for example, in the illustrated embodiments, different colors represent different durations of time since the last activation detected at the corresponding location. In embodiments, the raised bumps 614 may be configured to represent a location associated with an acquired electrical signal (e.g., an EGM), a virtual location associated with an aggregation of acquired electrical signals, and/or the like. As shown, the GUI 600 may also include a legend 626 configured to indicate the values represented by the annotation colors 616, 618, 620, 622, 624, and 626.

Figure 6B:
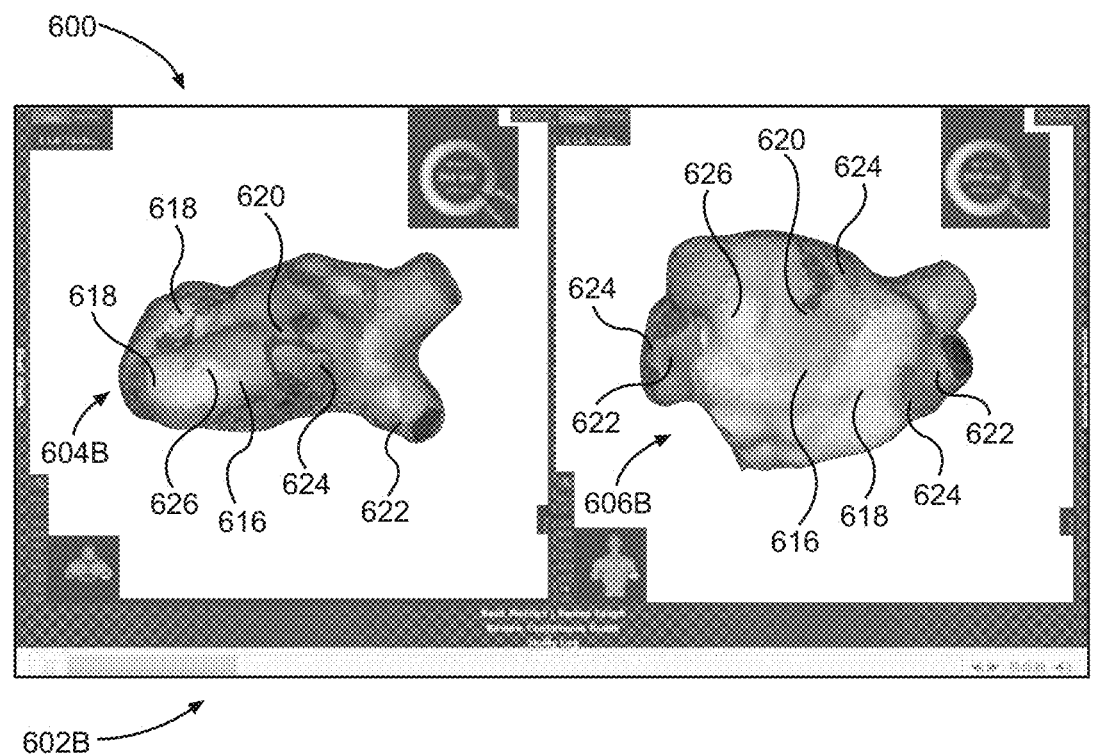
Figure 6C:
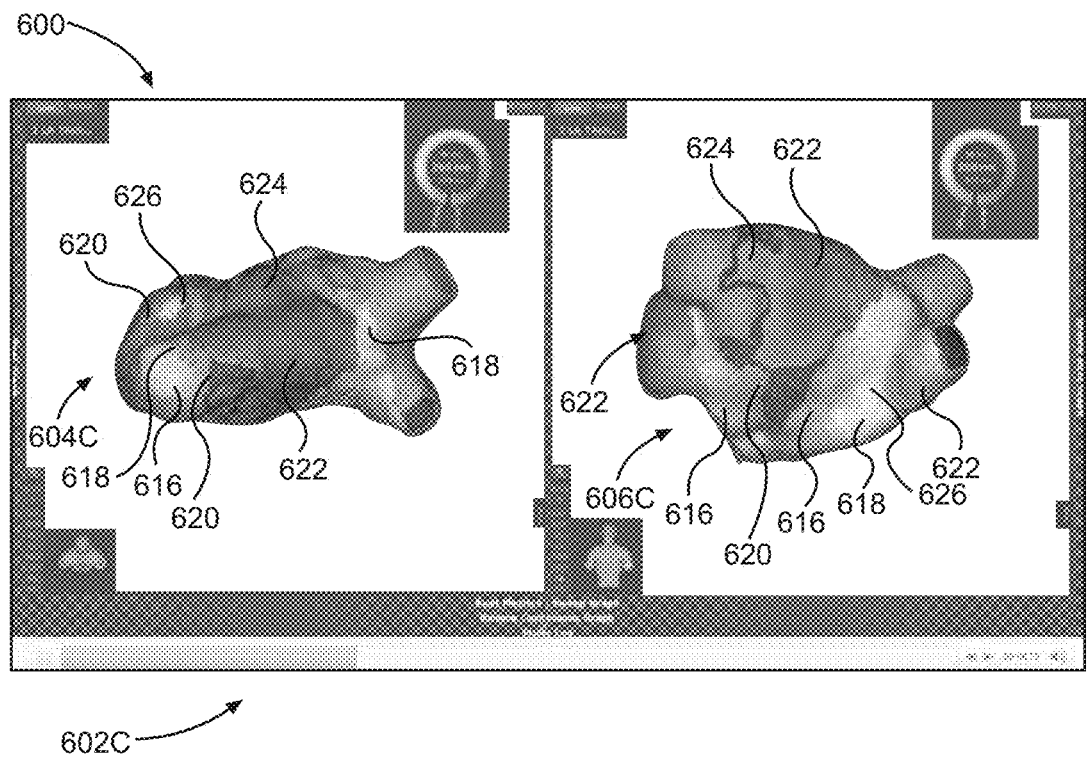
Figure 6D:
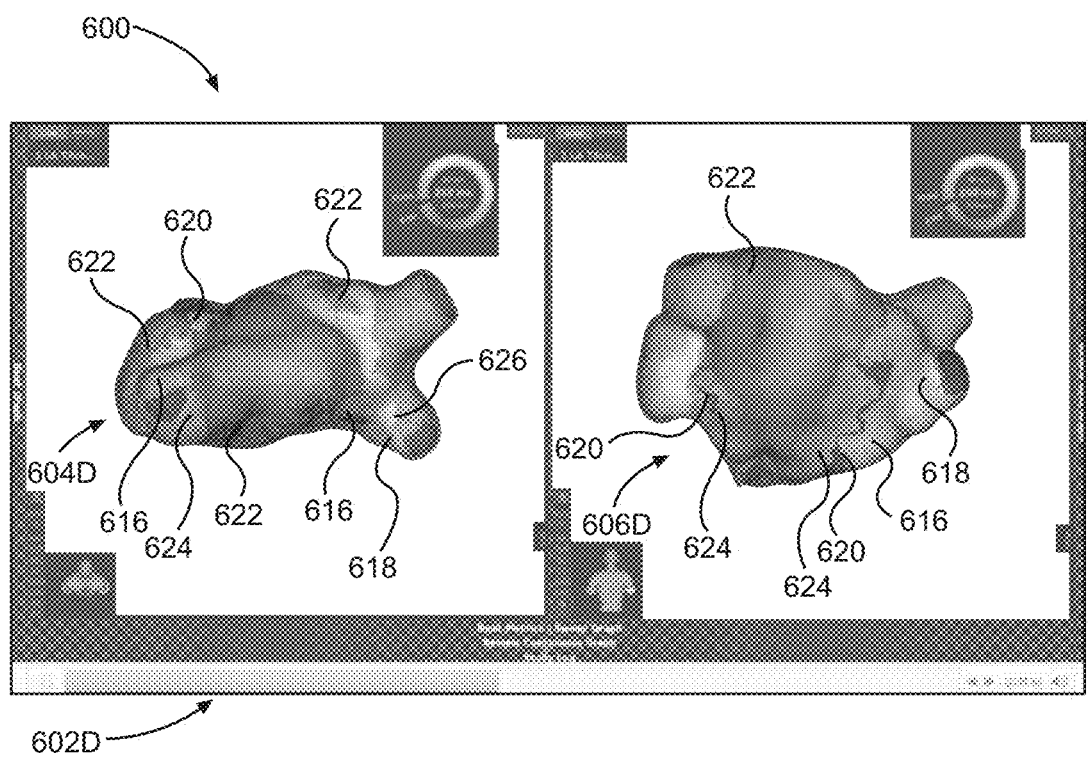

FIG. 6B depicts a second instance 602B of the GUI 600. The GUI 600 includes a first view 604B of the second instance 602B of the cardiac map and a second view 606B of the second instance 602B of the cardiac map. Similarly, FIG. 6C depicts a first view 604C and a second view 606C of a third instance 602C of the GUI 600, and FIG. 6D depicts a first view 604D and a second view 606D of a fourth instance 602D of the GUI 600. As illustrated in FIGS. 6A-6D, as an activation wavefront propagates through the cardiac structure, the color annotation associated with each region of the heart changes in response to algorithms configured to estimate, for each region, an amount of time since an activation was identified in the region. However, the nature of the larger swaths of color changing from one color to another without any clear boundaries can make such activation maps difficult to interpret. Additionally, the more complex algorithms for identifying activation times also may result in inaccuracies compared, for instance, to using the techniques described herein for identifying activations and generating an activation waveform. As such, embodiments facilitate presenting, on a cardiac map, a representation of a propagation of an activation waveform.

Figure 7A:
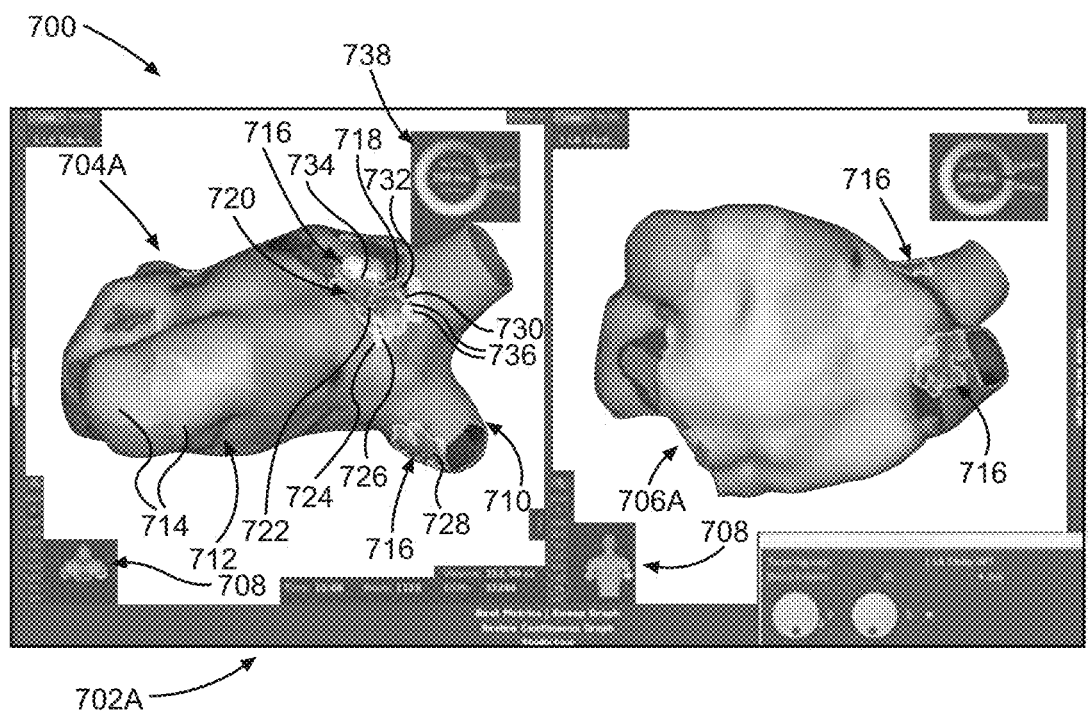
FIGS. 7A-7D depict instances of an illustrative GUI upon which is presented an activation waveform propagation map, in accordance with embodiments of the subject matter disclosed herein.

FIGS. 7A-7D depict illustrative screenshots from an interactive graphical user interface (GUI) 700 presented using a display device associated with a cardiac mapping system, showing views of an illustrative cardiac map, in accordance with embodiments of the subject matter disclosed herein. According to embodiments, the cardiac mapping system may be, be similar to, include similar features as, include, or be included within the mapping system 100 depicted in FIG. 1. The GUI 700 may be, be similar to, include similar features as, include, or be included within the GUI 600 depicted in FIGS. 6A-6D. FIG. 7A depicts a first instance 702A of the GUI 700. The GUI 700 includes a first view 704A of the first instance 702A of the cardiac map and a second view 706A of the first instance 702A of the cardiac map.

As shown, the first view 704A and the second view 706A represent two different orientations of the same cardiac map. In embodiments, the GUI 700 may be configured to present only one view of the cardiac map at a time. In embodiments, the GUI 700 may be configured to present, simultaneously, sequentially, and/or alternatively, any number of different views of any number of cardiac maps. In embodiments, for example, the GUI 700 may be configured to present a first cardiac map having annotations representing activations and a second cardiac map having annotations representing electrical potential, current density, and/or the like. As shown, an orientation indicator 708 may be configured to indicate the orientation, with respect to the body housing the heart, of the cardiac map that corresponds to the particular view 704A, 706A.

As shown in FIG. 7A, the cardiac map includes an anatomical shell 710 and annotations 712 displayed on the anatomical shell 710. In embodiments, the annotations 712 may represent any number of different metrics such as, for example, activations, voltages, impedance values, propagation velocity, current density, and/or the like. In embodiments, the map may be an activation map, on which some metric other than activations are indicated using a first set 714 of colors, and a propagating activation waveform is represented using a representation 716 of an activation region, which may be defined by a border 718 and a second set 720 of colors 722, 724, 726, 728, 730, 732, and 734. Although seven distinct colors are illustrated herein, any number of colors may be used for such representations.

As shown, the border 718 surrounding the representation 716 of the activation region may be rendered in a color that contrasts with the other colors used in the cardiac map so that the representation 716 of the activation region can be seen readily. For example, in embodiments, the border 718 may be white, red, yellow, and/or the like. In embodiments, a processing unit (e.g., the processing unit 200 depicted in FIG. 2) may be configured to dynamically adjust the color of the border 718 based on the surrounding colors as the representation 716 is propagated across the cardiac map. The activation region may represent a region of the tissue in which one or more activations are identified within a specified time period. In embodiments, individual activation locations may be indicated using representations 736 such as "Xs," raised bumps, and/or the like. In the illustrated embodiments, different colors of the representation of the activation wavefront propagation may still represent different durations of time since the last activation detected at the corresponding location. In other embodiments, the colors may represent activation durations, activation waveform amplitudes, voltage amplitudes associated with the activations, and/or the like. As shown, the GUI 700 may also include a legend 738 configured to indicate the values represented by the annotation colors 722, 724, 726, 728, 730, 732, and 734.

According to embodiments, the colors displayed within the representation 716 may be the same as the underlying annotation colors, but with a different display characteristic configured to highlight the representation. For example, the colors within the representation 716 may be displayed using a higher brightness level, contrast level, saturation level, and/or the like, as compared with the colors displayed outside of the representation 716. In this manner, facilitating highlighting regions of existing cardiac map may be accomplished without significant additional processing resources, as the algorithm may be configured to simply highlight an already-rendered representation of various annotations. In embodiments, the color hue of the colors displayed inside the representation 716 may be adjusted to highlight the region.

Figure 7B:
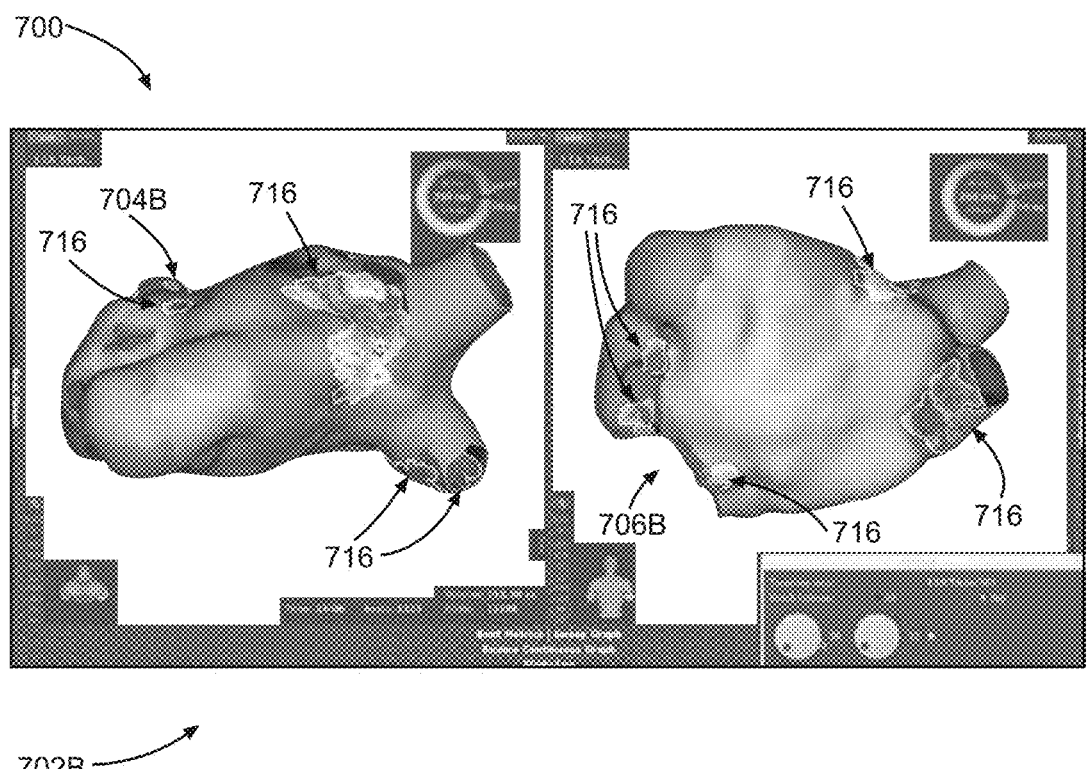
Figure 7C:
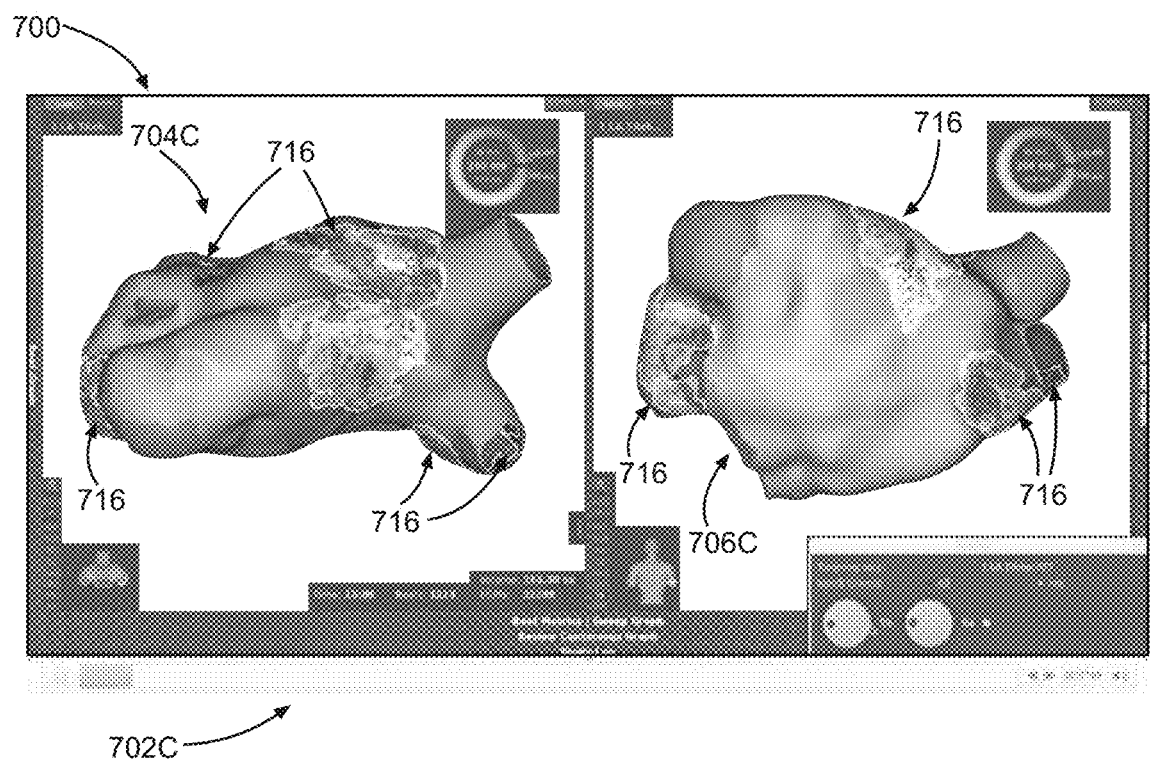
Figure 7D:
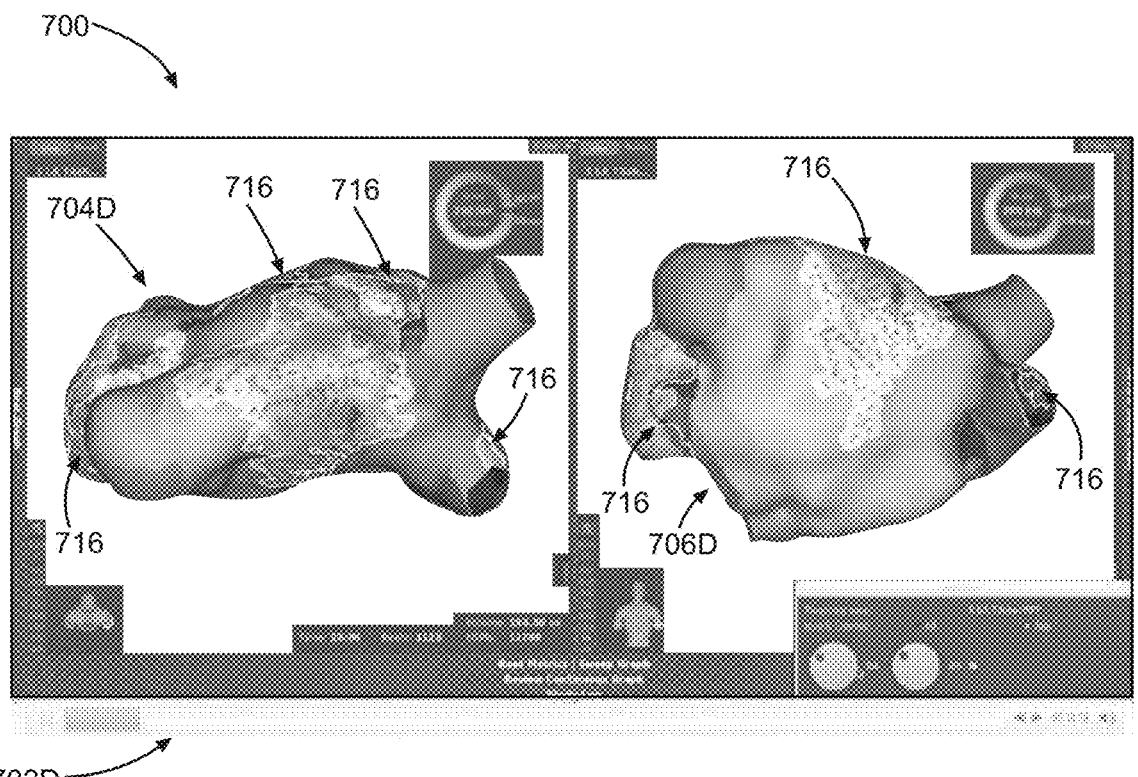

FIG. 7B depicts a second instance 702B of the GUI 700. The GUI 700 includes a first view 704B of the second instance 702B of the cardiac map and a second view 706B of the second instance 702B of the cardiac map. As shown, the location of the activation region 738A has changed, as have the locations of the colors 726A, 728A, 730A, 732A, and 734A within the border 736A, illustrating a propagating wavefront. The continued propagation of the activation wavefront is represented through FIGS. 7C and 7D, which depict a first view 704C and second view 706C of a third instance 702C of the GUI 800 and a first view 704D and a second view 706D of a fourth instance 702D of the GUI 700, respectively. As is evident from the illustrations in FIGS. 6A-6D and 7A-7D, the activation waveform propagation more clearly represents the propagation of an activation waveform throughout a cardiac structure, enabling more accurate diagnosis and interpretation. This is at least partially due to the fact that, as shown in FIGS. 7A-7D, embodiments of the disclosure facilitate sequentially highlighting (e.g., using brighter colors, different colors, a border, etc.) regions of activation over time.

The illustrative GUIs 600 and 700, shown in FIGS. 6A-6D and 7A-7D, respectively, are not intended to suggest any limitation as to the scope of use or functionality of embodiments of the present disclosure. Neither should the illustrative GUIs 600 and 700 be interpreted as having any dependency or requirement related to any single component or combination of components illustrated therein. Additionally, any one or more of the components depicted in FIGS. 6A-6D and 7A-7D may be, in embodiments, integrated with various ones of the other components depicted therein (and/or components not illustrated), all of which are considered to be within the ambit of the present disclosure.

Automatic EGM Classification

During electrophysiology (EP) procedures, clinicians often look for EGMs with disease-specific clinically-relevant characteristics, as identification of these EGMs may facilitate diagnosis, treatment optimization, and/or the like. These characteristics may include features such as, for example, isolated late potentials (ILPs), local abnormal ventricular activities (LAVAs), complex electrograms, fractionated electrograms, split electrograms, gap potentials, pre-potentials, and/or the like. While information like this is present in the electrical signals collected by conventional systems, it is often not readily accessible. Additionally, in embodiments, automatic electroanatomical mapping may result in the collection of more electrograms than can be manually inspected (e.g., between 6,000 and 20,000 electrograms, greater than 20,000 electrograms, etc.).

As indicated above, activation waveforms may facilitate automatic classification of electrical signals such as EGMs. In embodiments, a processing unit (e.g., the processing unit 120 depicted in FIG. 1 and/or the processing unit 200 depicted in FIG. 2) may be configured to perform an automatic classification technique, for example, to identify EGMs that fall within specified categories (also referred to as "classifications"). Categories may have associated parameters that may be used to further specify electrical signal characteristics to detect, such as duration of fractionation. In embodiments, this may facilitate quickly identifying EGMs of interest.

According to embodiments of the subject matter disclosed herein, a processing unit may be configured to automatically categorize EGMs, at least partially based on corresponding activation waveforms. In embodiments, the processing unit may be configured to instantiate an EGM classifier such as, for example, the EGM classifier 218 depicted in FIG. 2. The EGM classifier may include, for example, computer-executable instructions configured to cause a processor (e.g., the processor 202 depicted in FIG. 2) to implement a classifier that is configured to receive a set of input parameters and return a classification of an EGM with respect to one of any number of different categories. According to embodiments, the EGM classifier may be configured to implement classifiers sequentially, in parallel, in a nested fashion (e.g., classifying outputs of another classifier, classifying classified EGMs, etc.), and/or the like.

In embodiments, the input parameters may include, for example, an EGM, an activation waveform corresponding to the EGM, one or more additional relevant signals (e.g., a reference signal, an adjacent signal, etc.), physiological parameters (e.g., the patient's body temperature, the patient's blood pressure, etc.), environmental parameters (e.g., relative humidity, ambient temperature, presence of a magnetic field, etc.), device parameters (e.g., settings associated with the mapping system), and/or the like. In embodiments, one or more input parameters may be set, provided, and/or adjusted by a user (e.g., a clinician).

In embodiments, the EGM classifier may be configured to utilize a number of classifiers, each corresponding to one of a number of classification categories. In embodiments, classifiers may be supervised and/or unsupervised, and may include classifiers and/or classification techniques such as, for example, support vector machines (SVMs), neural networks, decision trees, k-nearest neighbor algorithms, quadratic classifiers, linear classifiers, and/or the like. According to embodiments, the EGM classifier may be configured to determine beat metrics, as explained above with regard to the beat metric determination step 306 of the illustrative method 300 depicted in FIG. 3. In embodiments, the classifications may be specified in the system, provided by a user, provided by another program component, provided by another computing device, and/or the like. In embodiments, the EGM classifier may be configured to return a classification decision, a confidence level associated with a classification decision, and/or the like.

According to embodiments, the processing unit may be configured to categorize each EGM collected during a mapping procedure. According to embodiments, the processing unit may be configured to provide a GUI that includes input features configured to facilitate receiving user selections of categories for display. In this manner, for example, embodiments may facilitate displaying annotations associated with only EGMs having a specified classification or classifications. In embodiments, the GUI may be configured to receive a classification search inquiry from a user, a computing device, and/or a program component. For example, in embodiments, a user may submit a classification search inquiry to identify EGMs having a specified classification. Upon identification of the EGMs satisfying the search query, the processing unit may be configured to display waveform representations of the identified EGMs, annotate a cardiac map with annotations (e.g., color, texture, image, etc.) corresponding to the identified EGMs. In this manner, embodiments facilitate enabling a user to adjust various parameters to find EGMs relevant to a procedure that the user is performing at the time.

According to embodiments, the EGM classifier may be configured to classify an EGM based, at least in part, on one or more activation waveforms corresponding to the EGM. In embodiments, for example, the processing unit may provide a GUI that includes selectable classification options such as, for example, selections of classifications that are based on activation waveform features. That is, for example, any number of different aspects of embodiments of the EGM classifier and/or other EGM categorization techniques described herein may include user-adjustable parameters, definitions, refinements, and/or the like. In this manner, embodiments facilitate a mapping system tool that enables the system to efficiently identify EGMs that have been automatically classified according to a user-selected classification. In embodiments, the EGM classifier may evaluate an activation waveform corresponding to an EGM to determine whether the activations included in the activation waveform satisfy one or more classification criteria. In this manner, embodiments facilitate classifying EGMs in a less computationally-burdensome manner than that of conventional systems since the EGM classifier evaluates the activation waveform to determine whether activations satisfy the one or more classification criteria, instead of, for example, performing morphology analysis on the EGM, template matching, and/or the like. Thus, for example, embodiments may facilitate identification of repeated activations and/or activation patterns over certain time durations that may be indicative of diseased tissue, even when the individual EGMs may not include readily-appreciated similarities.

As an example, in embodiments, a user may be interested in identifying EGMs having an isolated late potential (ILP), and may provide that information to a processing unit. In embodiments, if the system includes a classifier for classifying EGMs as having ILP, the processing unit may return identifiers corresponding to each of the EGMs having that classification. In embodiments, the system may, additionally or alternatively, include classifiers configured to classify EGMs as having certain characteristics that are associated with ILP. In the context of this example, the system may include a first classifier that classifies each EGM as either having two distinct activations or not having two distinct activations, and a second classifier that, for each EGM classified as having two distinct activations, classifies the EGM as being one in which the second activation occurs after the QRS complex. Upon receiving the query from the user, the processing unit may be configured to determine, based on the query, a number of EGM classifications, and/or combinations of classifications, that are relevant to the query, and to identify EGMs having those classifications and/or combinations of classifications.

As another example, a user may specify a classification search query configured to return complex EGMs. Upon receiving the search query, the EGM classifier may be configured to determine (e.g., based on a look-up table, language recognition, etc.) that, to satisfy the search query, an EGM would have an activation feature that lasts more than 25% of a mapping window, that activates at the end of, or after, the QRS complex, and that includes multiple peaks. In embodiments, the EGM classifier may identify EGMs that satisfy any combination of these characteristics, and may, in embodiments, assign weightings (e.g., confidence levels) to the EGMs based on their respective degrees of satisfaction of the characteristics. For example, an EGM that includes all three characteristics may be assigned a value of 1, while an EGM that includes only one or two of the characteristics may be assigned a value between 0 and 1. In embodiments, the weighting may be assigned based on the relationship of the particular characteristics to the search query. That is, for example, if the characteristic of activating at the end of, or after, a QRS complex is more unique to complex EGMs than is the characteristic of having multiple peaks, an EGM that includes the former may be assigned a higher weighting value than an EGM that includes the latter but not the former.

In embodiments, the EGM classifier may be configured to perform binary classifications and to process the search query simply by identifying each EGM that includes all of the specified characteristics. FIGS. 8A and 8B depict illustrative representations of a number of EGMs, in accordance with embodiments of the subject matter disclosed herein. The processing unit may determine, for example, that the first bipolar EGM 802 activates at the end of, or after, the QRS complex, and includes multiple peaks, but does not last more than 25% of the mapping window 804. The processing unit may determine, on the other hand, that the second bipolar EGM 806 activates at the end of, or after, the QRS complex, includes multiple peaks, and lasts more than 25% of the mapping window. Accordingly, the EGM classifier may be configured to return the second bipolar EGM in response to the search query, but not the first. In embodiments, the EGM classifier may be configured to return both the first and second EGMs, and assign each a confidence value based on a likelihood that the EGM is the type of EGM sought via the search query. According to embodiments, any number of various classifiers may be used to classify EGMs based on their corresponding activation waveforms, and representations of the classifications may be displayed, used for responding to user queries, and/or the like.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A system for facilitating display of cardiac information based on sensed electrical signals, the system comprising:
a display device configured to present a cardiac map of a cardiac structure; and
a processing unit configured to:
receive a set of electrical signals;
receive an indication of a measurement location corresponding to each electrical signal of the set of electrical signals;
generate an activation waveform corresponding to the set of electrical signals, wherein the activation waveform determines a probability for the each electrical signal to represent an activation of tissue at the corresponding measurement location;
generate, based on the activation waveform, a representation of a cardiac electrical signal feature;
facilitate presentation, on the display device, of the cardiac map and the representation of the cardiac electrical signal feature, wherein the cardiac map is an activation map that comprises representations of time durations since activations were detected at measurement locations of the cardiac map, wherein each of the time durations since activations were detected at the measurement locations are from a common previous activation;

receive a search query comprising a time step and an electrical signal characteristic;

identify any electrical signals included in the set of electrical signals having the electrical signal characteristic during the time step; and facilitate modification of the presentation of the cardiac map, via the display device, based on information associated with the identified electrical signals having the characteristic during the time step.

2. The system of claim 1, the representation of the cardiac electrical signal feature comprising a representation of an activation region, the activation region comprising a region of tissue in which one or more activations are identified within a specified time period.

3. The system of claim 2, the representation of the activation region comprising a border that is presented using a color that is different than one or more colors adjacent to the border, wherein the one or more adjacent colors are used to represent one or more annotations.

4. The system of claim 1, the map comprising a dynamic map, wherein the processing unit is further configured to cause the display device to sequentially present instances of the map corresponding to sequential time periods, wherein a location of the activation region changes throughout the sequential instances of the map, thereby representing a propagation of the activation waveform.

5. The system of claim 1, the plurality of electrical signals comprising a plurality of intracardiac electrograms (EGMs).

6. The system of claim 1, wherein the map comprises at least one of a voltage map, an activation map, and a fractionation map.

7. The system of claim 1, the cardiac electrical signal feature comprising at least one of an activation time, a minimum voltage value, a maximum voltages value, a maximum negative time-derivative of voltage, an instantaneous potential, a voltage amplitude, a dominant frequency, and a peak-to-peak voltage.

8. The system of claim 1, wherein the processing unit is further configured to automatically classify, based on the activation waveform, each electrical signal of the set of electrical signals.

9. The system of claim 1, wherein the processing unit is further configured to:

receive an indication of a user selection of one or more electrical signal characteristics;

identify a subset of the set of electrical signals having the one or more selected electrical signal characteristics;

generate, based on the identified subset of electrical signals, a spatial distribution of electrical signals having the one or more selected electrical signal characteristics; and facilitate presentation, on the display device, of a representation of the spatial distribution.

10. The system of claim 9, wherein the one or more selected electrical signal characteristics includes double-potentials, fractionation, multi-component, activation, lack of activation, split potentials, and/or QS signal morphology.

11. The system of claim 1, wherein to identify any electrical signals included in the set of electrical signals comprises assigning a confidence level to each of the identified electrical signals, wherein the confidence level corresponds to a likelihood an identified electrical signal of the identified electrical signals has the electrical signal characteristic.

12. A system for facilitating display of cardiac information based on sensed electrical signals, the system comprising:

a display device configured to present a cardiac map of a cardiac structure; and a processing unit configured to:

receive a set of electrical signals;

receive an indication of a measurement location corresponding to each electrical signal of the set of electrical signals;

generate an activation waveform corresponding to the set of electrical signals, wherein the activation waveform determines a probability for the each electrical signal to represent an activation of tissue at the corresponding measurement location;

classify, based on the activation waveform, each electrical signal of the set of electrical signals, wherein a classification of each electrical signal includes a confidence level associated with the classification;

receive an indication of a user selection of one or more electrical signal characteristics, wherein the one or more electrical signal characteristics correspond to time durations since activations were detected at measurement locations of the cardiac map, wherein the plurality of time durations since activations were detected at the measurement locations are from a common previous activation;

identify a subset of the set of electrical signals having the one or more selected electrical signal characteristics;

receive a classification search query and a time step;

identify one or more electrical signals of the subset of the set of electrical signals having the classification during the time step;

generate, based on the identified subset of electrical signals, a spatial distribution of the identified one or more electrical signals; and facilitate presentation, on the display device, of the cardiac map and a representation of the spatial distribution.

13. The system of claim 12, wherein the one or more selected electrical signal characteristics include double-potentials, fractionation, multi-component, activation, lack of activation, split potentials, and/or QS signal morphology.

14. The system of claim 12, wherein the representation of the spatial distribution comprises a dynamic representation of the one or more electrical signal characteristics.

15. A method of facilitating display of cardiac information, the method comprising:

receiving a set of electrical signals;

receiving an indication of a measurement location corresponding to each of the set of electrical signals;

generating an activation waveform corresponding to the set of electrical signals, wherein the activation waveform determines a probability for the each electrical signal to represent an activation of tissue at the corresponding measurement location;

generating, based on the activation waveform, a representation of a cardiac electrical signal feature;

facilitating presentation, on a display device, of a cardiac map and the representation of the cardiac electrical signal feature, wherein the cardiac map is an activation map that comprises representations of time durations since activations were detected at measurement locations of the cardiac map, wherein each of the time durations since activations were detected at the measurement locations are from a common previous activation;

receiving a search query comprising a time step and an electrical signal characteristic;

identifying any electrical signals included in the set of electrical signals having the electrical signal characteristic during the time step; and facilitating modification of the presentation of the cardiac map, via the display device, based on information associated with the identified electrical signals having the characteristic during the time step.

16. The method of claim 15, the representation of the cardiac signal feature comprising a representation of an activation region, the activation region comprising a region of tissue in which one or more activations are identified within a specified time period.

17. The method of claim 16, the map comprising a dynamic map, the method further comprising causing the display device to sequentially present instances of the map corresponding to sequential time periods, wherein a location of the activation region changes throughout the sequential instances of the map, thereby representing a propagation of the activation waveform.

18. The method of claim 15, further comprising automatically classifying, based on the activation waveform, each electrical signal of the set of electrical signals.

19. The method of claim 15, further comprising:

receiving an indication of a user selection of one or more electrical signal characteristics;

identifying a subset of the set of electrical signals having the one or more selected electrical signal characteristics;

generating, based on the identified subset of electrical signals, a spatial distribution of electrical signals having the one or more selected electrical signal characteristics; and facilitating presentation, on the display device, of a representation of the spatial distribution.

20. The method of claim 15, identifying any electrical signals included in the set of electrical signals comprises assigning a confidence level to each of the identified electrical signals, wherein the confidence level corresponds to a likelihood an identified electrical signal of the identified electrical signals has the electrical signal characteristic.

* * * * *